(12) United States Patent
Jauregui Johnston et al.

(10) Patent No.: US 12,178,496 B2
(45) Date of Patent: Dec. 31, 2024

(54) TREATMENT OF DERMAL GLANDS BY THE APPLICATION OF NON-THERMAL ENERGY

(71) Applicant: PULSE BIOSCIENCES, INC., Hayward, CA (US)

(72) Inventors: Lauren M. Jauregui Johnston, Millbrae, CA (US); Edward A. Ebbers, San Carlos, CA (US); David J. Danitz, San Jose, CA (US); Richard L. Nuccitelli, Millbrae, CA (US); Darrin R. Uecker, San Mateo, CA (US); Kevin L. Moss, Lathrop, CA (US); Cameron D. Hinman, Thurmond, NC (US)

(73) Assignee: Pulse Biosciences, Inc., Hayward, CA (US)

(*) Notice: Subject to any disclaimer, the term of this patent is extended or adjusted under 35 U.S.C. 154(b) by 905 days.

(21) Appl. No.: 17/284,029

(22) PCT Filed: Oct. 9, 2019

(86) PCT No.: PCT/US2019/055486
§ 371 (c)(1),
(2) Date: Apr. 9, 2021

(87) PCT Pub. No.: WO2020/077019
PCT Pub. Date: Apr. 16, 2020

(65) Prior Publication Data
US 2022/0008122 A1 Jan. 13, 2022

Related U.S. Application Data

(60) Provisional application No. 62/744,027, filed on Oct. 10, 2018.

(51) Int. Cl.
*A61B 18/12* (2006.01)
*A61B 18/14* (2006.01)
(Continued)

(52) U.S. Cl.
CPC .......... *A61B 18/1477* (2013.01); *A61B 34/30* (2016.02); *A61B 2017/00172* (2013.01);
(Continued)

(58) Field of Classification Search
CPC ............ A61B 18/1477; A61B 18/1206; A61B 18/148; A61B 2017/00747;
(Continued)

(56) References Cited

U.S. PATENT DOCUMENTS 5,964,726 A 10/1999 Korenstein et al.
6,241,701 B1 6/2001 Hofmann
(Continued)

FOREIGN PATENT DOCUMENTS

KR 101220541 B1 1/2013
KR 101636365 B1 7/2016
(Continued)

OTHER PUBLICATIONS

Gundersen et al.; Nanosecond pulse generator using a fast recovery diode; IEEE; InProceedings of the 26th Inernational Pulsed Modulator Conference; 603-606; (year of pub. sufficiently earlier than effective US filling date and any foreign priority date) 2004.
(Continued)

*Primary Examiner* — Thomas A Giuliani
(74) *Attorney, Agent, or Firm* — Shay Glenn LLP

(57) ABSTRACT

Described herein are methods and apparatuses for reducing or eliminating skin glands (e.g., sebaceous, eccrine and apocrine) with an electric treatment. These apparatuses and methods may produce electroporation of cells by applying treatment dose having an energy density sufficient to elimi-
(Continued)

nate or reduce the size of a target gland. Also described herein are methods for treating and/or preventing a disorder of a skin gland. For example, described herein are methods of treating sebaceous hyperplasia.

22 Claims, 19 Drawing Sheets

(51) Int. Cl.
    *A61B 34/30*     (2016.01)
    *A61B 17/00*     (2006.01)
    *A61B 18/00*     (2006.01)

(52) U.S. Cl.
    CPC .............. *A61B 2017/00747* (2013.01); *A61B 2018/00083* (2013.01); *A61B 2018/00458* (2013.01); *A61B 2018/00577* (2013.01); *A61B 2018/00702* (2013.01); *A61B 2018/00761* (2013.01); *A61B 2018/00767* (2013.01); *A61B 2018/143* (2013.01); *A61B 2018/1475* (2013.01)

(58) Field of Classification Search
    CPC ........... A61B 2018/00458; A61B 2018/00577; A61B 2018/00702; A61B 2018/00761; A61B 2018/00767; A61B 2018/143; A61B 2018/1475; A61B 2018/0016; A61B 2018/00452; A61B 2018/1425; A61B 2018/1427; A61B 90/04; A61N 1/36017; A61N 1/0502
    USPC .... 606/34, 40–42, 49; 607/98, 99, 109, 113, 607/115, 116
See application file for complete search history.

(56) References Cited

U.S. PATENT DOCUMENTS

| | | | |
|---|---|---|---|
| 6,326,177 B1 | 12/2001 | Schoenbach et al. | |
| 6,366,808 B1 | 4/2002 | Schroeppel et al. | |
| 7,267,676 B2 | 9/2007 | Chornenky et al. | |
| 7,395,112 B2 | 7/2008 | Keisari et al. | |
| 8,000,813 B2 | 8/2011 | Schoenbach et al. | |
| 8,512,334 B2 | 8/2013 | Nuccitelli et al. | |
| 8,822,222 B2 | 9/2014 | Beebe et al. | |
| 9,101,764 B2 | 8/2015 | Nuccitelli et al. | |
| 9,445,767 B2 | 9/2016 | Abreu | |
| 9,656,055 B2 | 5/2017 | Weissberg et al. | |
| 9,724,155 B2 | 8/2017 | Nuccitelli et al. | |
| 9,956,391 B2 | 5/2018 | Weissberg et al. | |
| 10,252,050 B2 | 4/2019 | Kreis et al. | |
| 10,850,095 B2 | 12/2020 | Ebbers et al. | |
| 10,857,347 B2 | 12/2020 | Danitz et al. | |
| 2002/0010491 A1* | 1/2002 | Schoenbach | A61B 18/1206 607/2 |
| 2003/0018370 A1 | 1/2003 | King et al. | |
| 2006/0264807 A1 | 11/2006 | Westersten et al. | |
| 2010/0038971 A1 | 2/2010 | Sanders et al. | |
| 2010/0049178 A1* | 2/2010 | Deem | A61B 18/1477 606/1 |
| 2010/0262135 A1* | 10/2010 | Berube | A61B 18/1477 606/33 |
| 2011/0009807 A1 | 1/2011 | Kjeken et al. | |
| 2011/0092973 A1 | 4/2011 | Nuccitelli et al. | |
| 2013/0012937 A1 | 1/2013 | Mulier et al. | |
| 2013/0026137 A1 | 1/2013 | Kindel et al. | |
| 2014/0249361 A1 | 9/2014 | DiUbaldi et al. | |
| 2014/0364797 A1 | 12/2014 | Schoenbach et al. | |
| 2015/0201991 A1 | 7/2015 | Zemlin | |
| 2017/0080221 A1 | 3/2017 | Dai | |
| 2017/0245928 A1 | 8/2017 | Xiao et al. | |
| 2017/0246455 A1 | 8/2017 | Athos et al. | |
| 2017/0319851 A1 | 11/2017 | Athos et al. | |
| 2018/0078755 A1 | 3/2018 | Kreis et al. | |
| 2018/0103991 A1* | 4/2018 | Linhart | A61B 18/1477 |
| 2018/0243558 A1 | 8/2018 | Athos et al. | |
| 2019/0217080 A1 | 7/2019 | Moss et al. | |

FOREIGN PATENT DOCUMENTS

| | | |
|---|---|---|
| WO | WO2010/098784 A1 | 9/2010 |
| WO | WO2017/117508 A1 | 7/2017 |

OTHER PUBLICATIONS

Nuccitelli et al.; First?in?human trial of nanoelectroablation therapy for basal cell carcinoma: proof of method; Experimental Dermatology; 23(2); pp. 135-137; Feb. 2014.
Tang et al.; Diode Opening Switch Based Nanosecond High Voltage Pulse Generators for Biological and Medical Applications; IEEE Transactions on Dielectrics and Electrical Insulation; 14(4); pp. 878-883; Aug. 2007.
Wang et al.; Solid-State High Voltage Nanosecond Pulse Generator; IEEE InPulsed Power Conference;pp. 1199-1202; 4 pages; Jun. 13, 2005.
Australian Application No. 2019358073, Examination Report No. 1 mailed Aug. 23, 2021; 5 pages.
European Supplemental Search Report mailed Nov. 19, 2021 for European Patent Application No. 19871481.8; 10 pages.
Imayama; Long-and short-term histological observations of congenital nevi treated with the normal-mode ruby laser; Archives of dermatology; 135(10); pp. 1211-1218; Oct. 1, 1999.
International Search Report and Written Opinion mailed Jan. 31, 2020 for PCT/US2019/055486; 11 pages.
Preliminary Report on Patentability mailed Apr. 22, 2021 for PCT/US2019/055486; 8 pages.

* cited by examiner

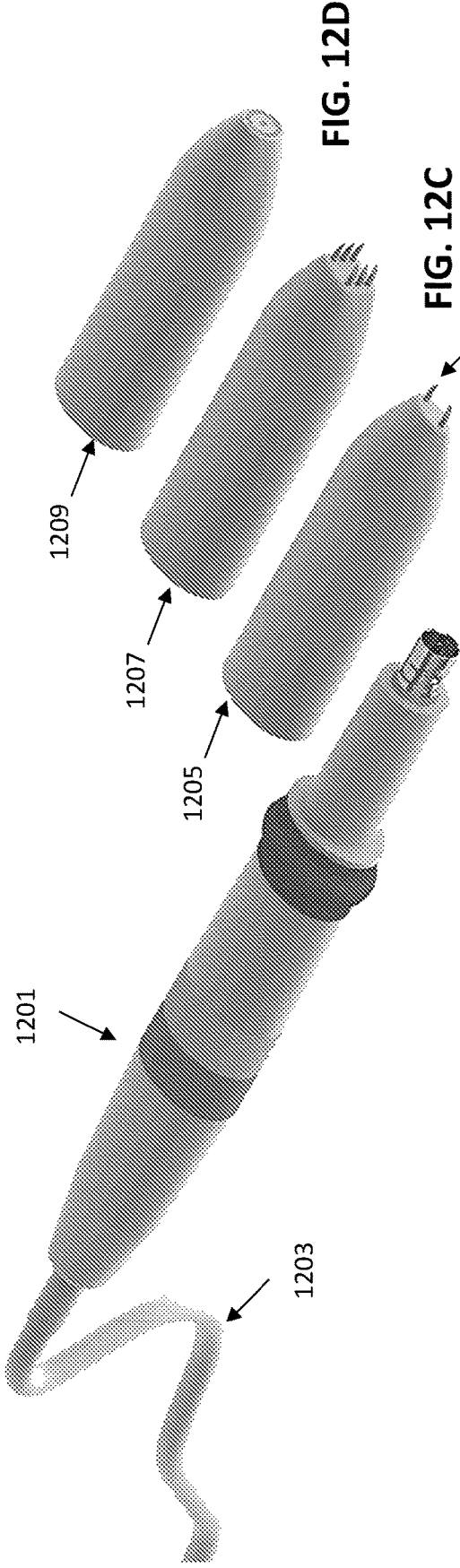
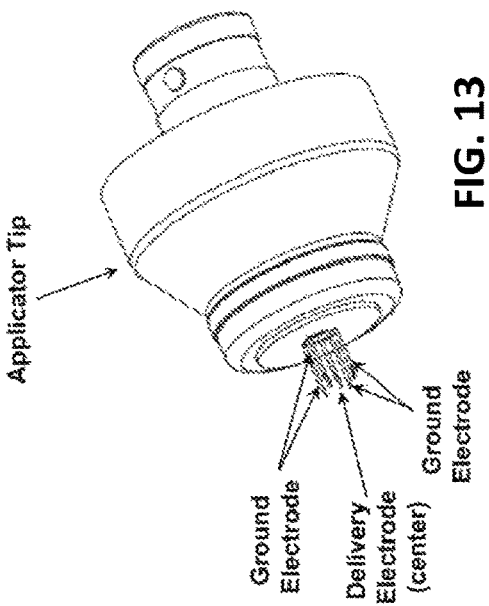

1.5 mm tip 2.5 mm By 2.5 mm Tip with ficucials

| Electrode Dimensions | | | Amplitude (kV) | Pulse Width (ns) | Frequency (Hz) | Number of Pulses | Treatment Time (s) | Power (energy per s) (Watts) | Total Energy Density (J/mm^3) |
|---|---|---|---|---|---|---|---|---|---|
| Length (mm) | Width (mm) | Depth (mm) | | | | | | | |
| 1.5 | 1.5 | 2 | 3 to 4 | 200 to 300 | 4 to 8 | 100 to 500 | 12 to 125 | 0.01 to 0.06 | 0.08 to 0.9 |
| 2.5 | 2.5 | 2 | 6 to 8 | 200 to 300 | 4 to 8 | 50 to 200 | 6 to 50 | 0.04 to 0.4 | 0.06 to 0.7 |
| 5 | 5 | 2 | 12 to 15 | 200 to 300 | 2 to 8 | 30 to 70 | 4 to 35 | 0.2 to 3 | 0.03 to 0.5 |

| Spot Size | Treatment Level (Joules) | Treated Lesions N=380 | Efficacy % 60 Days Post-TX INTERIM Results, N=210 |
|---|---|---|---|
| 2.5 mm Tip (N=245) | 0.4 J | 91 | 96% |
| | 0.7 J | 52 | 90% |
| | 1.6 J | 88 | 98% |
| | 3.1 J | 14 | 86%[2] |

TREATMENT OF DERMAL GLANDS BY THE APPLICATION OF NON-THERMAL ENERGY

CROSS REFERENCE TO RELATED APPLICATIONS

This patent application is a national phase application under 35 USC 371 of International Patent Application No. PCT/US2019/055486, titled "TREATMENT OF DERMAL GLANDS BY THE APPLICATION OF NON-THERMAL ENERGY," filed Oct. 9, 2019, now International Publication No. WO 2020/077019, which claims priority to U.S. Provisional Patent Application No. 62/744,027, titled "TREATMENT OF DERMAL GLANDS BY THE APPLICATION OF NON-THERMAL ENERGY" and filed on Oct. 10, 2018, which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

Specifically incorporate by reference in their entirety are each of: U.S. patent application Ser. No. 15/973,254, filed May 7, 2018, which claims priority to U.S. provisional patent application No. 62/542,711, filed Aug., 8, 2017; U.S. patent application Ser. No. 13/631,618 filed Sep. 28, 2012 (now U.S. Pat. No. 9,656,055), U.S. patent application Ser. No. 13/710,077, filed Dec. 12, 2012 (now U.S. Pat. No. 9,956,391); PCT patent application published as WO 2018053539 on Mar. 22, 2018; U.S. patent application Ser. No. 15/920,389, filed on Mar. 13, 2018, which claims priority to U.S. provisional patent application No. 62/618,022, filed on Jan. 16, 2018; and U.S. provisional patent application No. 62/642,552, filed on Mar. 13, 2018.

FIELD

This disclosure relates to treatment of tissue by the application of pulsed electric fields, such as nanosecond electrical pulses. The treatment may selectively and specifically ablate glands, including but not limited to sebaceous glands, eccrine glands and apocrine glands, without provoking a significant inflammatory response, and while sparing the adjacent non-cellular tissue.

BACKGROUND

The application of destructive modalities for the treatment of tissue, and in particular, for the treatment of glands within the tissue, is well known for both cosmetic and therapeutic treatments. For example, many skin treatments, including treatment of skin disorders, by the application of thermal modalities are widely used in dermatology. Thermal treatments in particular, including the use of liquid nitrogen (e.g., −196° C. to −210° C.) have been used to treat or remove affected skin, but may result in severe disruption and immediate necrosis of skin cells and bursting of the cell membrane, leading to an acute inflammation response, loss of melanocytes, and damage to the dermis, that can result in scar tissue formation and an abnormal appearance.

Other thermal treatment modalities that result in tissue destruction include tissue heating generated by laser or radio frequency devices which may effectively burn the tissue (including skin) and may cause immediate cell necrosis and destruction of cell membranes and may also provoke an inflammatory response and suffer from the same drawbacks as extreme cold. It would be beneficial to provide therapies, and in particular, non-thermal therapies, which produce a minimal, if any, local inflammatory response. As applied to dermal tissue, it would be particularly helpful to provide for the formation of new epidermal tissue with reduced or no significant scarring and a normal appearance after restoration of the epidermal surface after a normal healing period.

Very short (e.g., nanosecond range), high-field strength electric pulses have been described for electroperturbation of biological cells. For example, electric pulses may be used in treatment of human cells and tissue including tumor cells, such as basal cell carcinoma, squamous cell carcinoma, and melanoma. See, e.g., Nuccitelli et al. (2014) "First-in-human trial of nanoelectroablation therapy for basal cell carcinoma: proof of method." *Exp Dermatol* 23:135-7, incorporated herein by reference it its entirety.

The voltage induced across a cell membrane may depend on the pulse length and pulse amplitude. Pulses longer than about 1 microsecond may charge the outer cell membrane and lead to opening of pores. Permanent openings may result in instant or near instant cell death. Pulses shorter than about 1 microsecond may affect the cell interior and result in a delayed cell death with intact cell membranes. Such shorter pulses with a field strength varying, for example, in the range of 0.1 kV/cm to 1000 kV/cm (e.g., 10 kV/cm to 100 kV/cm) may trigger apoptosis (i.e. programmed cell death) in some or all of the cells exposed to the described field strength and pulse duration. These higher electric field strengths and shorter electric pulses may be useful in manipulating intracellular structures, such as nuclei and mitochondria.

Nanosecond high voltage pulse generators have been proposed for biological and medical applications. For example, see: Gundersen et al. "Nanosecond Pulse Generator Using a Fast Recovery Diode", IEEE 26th Power Modulator Conference, 2004, pages 603-606; Tang et al. "Solid-State High Voltage Nanosecond Pulse Generator," IEEE Pulsed Power Conference, 2005, pages 1199-1202; Tang et al. "Diode Opening Switch Based Nanosecond High Voltage Pulse Generators for Biological and Medical Applications", IEEE Transactions on Dielectrics and Electrical Insulation, Vol. 14, No. 4, 2007, pages 878-883; Schoenbach et al. "Method and Apparatus for Intracellular Electro-Manipulation", U.S. Pat. No. 6,326,177; and Sanders et al. "Nanosecond Pulse Generator", U.S. Pat. No. 8,115,343. The entire content of these publications is incorporated herein by reference.

There is a need for development of the treatments and/or prevention of disorders of skin glands including sebaceous glands, eccrine glands and apocrine glands. There is also a need for cosmetic treatments that may include reducing or eliminating glands, including sebaceous glands, eccrine glands and apocrine glands.

SUMMARY OF THE DISCLOSURE

The methods, systems and apparatuses described herein generally describe the application of pulsed electric energy treatment(s) to dermal tissue to reduce the size and/or number of glands (e.g., one or more of sebaceous, eccrine and apocrine glands) in a defined region of skin. These methods, systems and apparatuses may specifically target sebaceous glands, eccrine glands and apocrine glands, for example, within the dermis layer of the skin, while avoid causing damage to the structures outside of the targeted region of the skin, for example, portions of epidermis and dermis. The methods, system and devices of the present disclosure may use short, high field strength electric pulses, for example, pulses of sub-microsecond duration. Although for convenience of description sebaceous glands in particular are described as a possible target of the methods and apparatuses described herein, however it should be noted that the disclosure is not limited to such glands and any other glands (e.g., eccrine and apocrine glands) may also or alternatively be targeted.

In general, the methods and apparatuses described herein apply pulsed electrical energy to a region of skin including one or more glands at an energy level (e.g., at an energy density level within the tissue) that is above a threshold for eliminate all or some of the glands in the targeted region of the skin. In some variations the pulsed electrical energy is applied very fast, so that the pulses have a pulse width within the nanosecond range (e.g., between 0.1 ns and 1000 ns). The energy may have a high-field strength and may be applied to specifically targeted regions of the skin including regions of skin including one or more glands. Surprisingly, energy applied below the threshold may not result in the destruction of the glands, although such levels may be sufficient for other therapies that rely on the application of pulsed electrical energy within the nanosecond range (e.g., nanosecond pulse therapies), including other skin therapies. The methods and apparatuses described herein may eliminate, either completely or partially, all or some of the gland within the target tissue region. In some variations, eliminated glands may be destroyed, so that the cell body, and gland structures are destroyed.

The energy density applied to the region of the skin may depend in part on the geometry of the plurality of electrodes. In some variations, the energy density applied to the region of skin may be between about 0.03 J/mm$^3$ and about 0.9 J/mm$^3$ for an array of electrodes forming a pattern having a width and a height of between 1.4 mm and 5.5 mm. For example, the energy density applied to the region of skin may be between about 0.03 J/mm$^3$ and about 0.5 J/mm$^3$ for an array of electrodes forming a pattern having a width and a height of between about 4 mm and about 6 mm. In some variations, the energy density applied to the region of skin may be between about 0.06 J/mm$^3$ and about 0.7 J/mm$^3$ for an array of electrodes forming a pattern having a width and a height of between about 2 mm and about 3 mm. In some variations, the energy density applied to the region of skin is between about 0.08 J/mm$^3$ and about 0.9 J/mm$^3$ for an array of electrodes forming a pattern having a width and a height of between about 1 mm and about 2 mm. The pattern of electrodes refers to the arrangement of electrodes in contact with the tissue, and may be any appropriate shape (e.g., a square, rectangle, circle, triangle, etc.), which may be formed by the electrodes, including the space between the electrodes. The dimensions of this pattern may include the electrodes. In some variations the energy density applied to the region of skin may be reduced by between about 80-90% (e.g., about 85%), which may reduce side effects, such as hyperpigmentation and volume loss. Thus, in some variations the energy density applied to the region of skin may be between about 0.003 J/mm$^3$ and about 0.09 J/mm$^3$ for an array of electrodes forming a pattern having a width and a height of between 1.4 mm and 5.5 mm. For example, the energy density applied to the region of skin may be between about 0.003 J/mm$^3$ and about 0.05 J/mm$^3$ for an array of electrodes forming a pattern having a width and a height of between about 4 mm and about 6 mm. In some variations, the energy density applied to the region of skin may be between about 0.006 J/mm$^3$ and about 0.070 J/mm$^3$ for an array of electrodes forming a pattern having a width and a height of between about 2 mm and about 3 mm. In some variations, the energy density applied to the region of skin is between about 0.008 J/mm$^3$ and about 0.090 J/mm$^3$ for an array of electrodes forming a pattern having a width and a height of between about 1 mm and about 2 mm.

Although the examples and illustrations described herein typically relate to the application of pulsed electrical energy in the nanosecond range, in some variation the energy may instead be applied in the picosecond (e.g., between 0.1 ps and 1000 ps) and/or microsecond (e.g., between 1 microsecond and 1000 microseconds) ranges, or other pulse width ranges, including variable pulse width ranges.

For example, described herein are methods (e.g., treatment methods) that generally include: applying a plurality of electrodes against the subject's skin so that at least a portion a subject's skin (a target region of the subject's skin) that includes a target gland is between two or more of the plurality of electrodes; applying pulsed electrical energy (for example, having a pulse duration in sub-microsecond pulse range) between two or more of the plurality of the electrodes, wherein the pulsed electrical energy provides an energy density sufficient to eliminate the target gland without permanently damaging structures outside the target gland.

The step of applying electrodes against the subject's skin may include inserting a plurality of electrodes into a subject's skin so that a region of skin including a target gland is between two or more of the plurality of electrodes. Alternatively, applying the electrodes may include applying non-penetrating electrodes against the skin. For example, in some variations the skin may be pinched or gripped between two or more electrodes on the surface of the skin.

The energy density applied to the region of skin may be within a range that is sufficient to eliminate the gland, such as, for example, between about 0.001 J/mm$^3$ and about 1.5 J/mm$^3$ (e.g., between about 0.003 J/mm$^3$ and about 0.9 J/mm$^3$). Outside of the range that is sufficient for particular application, the gland may not be eliminated or destroyed, or the gland may not be eliminated without damaging adjacent tissues. The structures outside the target gland may comprise one or more of: a portion of epidermis above the target gland, a portion of epidermis adjacent the target gland, one or more portions of dermis adjacent the target gland.

In any of these variations, the pulsed electrical energy may provide an energy density sufficient to eliminate a full length of the targeted gland. Even when the energy is applied to a region of the gland (e.g., the cell body region), the energy may result in elimination of the entire gland.

For example, described herein are methods comprising: inserting a plurality of electrodes into a subject's skin so that a region of skin including a target gland is between two or more of the plurality of electrodes; and applying pulsed electrical energy having a pulse duration in sub-microsecond pulse range between the two or more of the plurality of electrodes, wherein the pulsed electrical energy provides an energy density sufficient to eliminate the target gland without permanently damaging structures outside the target gland. These methods may be methods of selectively eliminating one or more glands within a region of skin.

In some variations, the electrodes used are needle electrodes that may be positioned on either side of the portion of skin including the gland(s), such as a dysfunctioning gland or glands that are to be eliminated. The electrodes may be part of an array of tissue penetrating needles (e.g., blades, needles, plates, etc.). The electrodes may be partially insulated, so that only a base portion of the needle electrode (such as a portion that is closest to the surface of the skin, when the needle electrode is inserted into the skin) is insulated. The insulated portion of the electrode may be, for example, from 5% to 90% of the length of the needle electrode. Depending on a depth of the location of the target gland and/or a length of the needle electrode, the depth of the insulated portion is selected to protect the upper layer of the skin, e.g., to protect at least a portion of epidermis that is above the targeted gland. For example, when the targeted gland begins at approximately 1 mm below the surface of the skin, the distal portion of the length of the needle electrode that is deeper than 1 mm beneath the skin surface when inserted into the skin may be uninsulated. As mentioned, the electrodes may be part of an array of tissue penetrating needles (e.g., blades, needles, plates, etc.). For example, inserting the plurality of electrodes into the subject's skin may comprise inserting an array of needle electrodes into the skin. In some variations, each needle electrode of the plurality of electrodes comprises an insulated base portion and uninsulated tip portion. For example, inserting the plurality of electrodes may include inserting the electrodes such that insulated portions of each of the plurality of electrodes extend between 0.1 and 1 mm below a surface of the skin.

In some variations the applicator tips may include a retractable treatment tip housing that is configured to retract to expose the needle electrodes. The housing may be deflected proximally as the applicator tip is pushed against the skin. In such variations the base of the treatment tip is the outer surface of the retractable housing that pushes against the skin. The base region of the electrode may be insulated and may be exposed when the retractable housing is fully retracted (e.g., pushed against the skin). In any of the methods and apparatuses described herein the treatment tip may be configured to include short needle electrodes, e.g., having a fully extended length, which may be inserted into the skin tissue, of 2 mm or less (e.g., 1.75 mm or less, 1.5 mm or less, 1.25 mm or less, 1 mm or less, 0.9 mm or less, 0.8 mm or less, 0.7 mm or less, 0.6 mm or less, 0.5 mm or less, etc.).

Inserting the plurality of electrodes into the subject's skin may comprise inserting the plurality of electrodes into the subject's skin so that one or more of a sebaceous gland, an eccrine gland or an apocrine gland is the region of skin. Applying (e.g., inserting) the plurality of electrodes may comprise inserting the plurality of electrodes around a sebaceous hyperplasia lesion wherein the plurality of electrodes is applied into the subject's skin by inserting the plurality of electrodes so that the sebaceous hyperplasia lesion within the subject's skin is between two or more of the plurality of electrodes. As mentioned, the target gland may be at least one of a sebaceous gland, an eccrine gland, an apocrine gland, or any other gland.

The methods described herein may be configured to minimally disrupt the skin tissue, other than the glands in the tissue. For example, applying may include applying a non-thermal treatment that does not disrupt the cell membrane of the epidermal cells.

The applied electrical pulses may have any appropriate parameter values (e.g., frequency, pulse width, amplitude, etc.), so long as the energy delivered to the tissue is above the threshold for eliminating a gland in the skin tissue. For example, applying may comprise applying the pulsed electrical energy between the plurality of electrodes, wherein pulses of the pulsed electrical energy have a peak field strength of at least 0.1 kV/cm (e.g., 1 kV/cm, 5 kV/cm, 10 kV/cm, etc.).

Any appropriate dose parameter may be used for treatment. For example, the methods may include applying a single treatment dose extending for a treatment time (e.g., 20 minutes or less, 15 minutes or less, 10 minutes or less, 5 minutes or less, etc., between 1 second and 20 minutes, between 1 second and 10 minutes, between 1 second and 5 minutes, etc.). For example, the method may comprise applying treatment for 5 minutes or less (e.g., 3 minutes or less, 2 minutes or less, 1 minute or less, 50 seconds or less, 45 seconds or less, 40 seconds or less, 35 seconds or less, 30 seconds or less, than 25 seconds or less, 20 seconds or less, etc.). In some variations the number of pulses applied during treatment may be between, for example, 10 and 5000 (e.g., between 10-2000, between 10-1500, between 10-1000, between 10-500, between 10-250, between 10-200, between 10-175, less than 5000, less than 4000, less than 3000, less than 2000, less than 1000, less than 500, less than 300, less than 200, etc.) For example, the method may include applying less than 1000 pulses.

Repeated dosing may not be necessary, although in some variations additional (repeated) treatments may be applied to the same region of tissue. In some variations the same region of tissue may not be re-treated until after a waiting period of, e.g., 1 day, 4 days, 7 days, etc. For example, any of these methods may include allowing the region of skin to recover, for example, for 1 week before reapplying electrical energy to the region.

In general, the methods described herein may be used to treat any disorder related to the dysfunction of a gland in the skin. For example, any of methods described herein may be methods of treating (or preventing) one or more of: acne (acne vulgaris, cystic acne), oily skin, rosacea, rosacea-like dermatitis, lupus miliaris disseminatus faciei (LMDF), xerosis, asteatosis, seborrhea, seborrheic dermatitis, seborrheic-like psoriasis, steatocystoma, hyperhidrosis, bromhidrosis/osmidrosis, chromhidrosis, hidradenitis suppurativa, Fox Fordyce disease, Frey's syndrome, cysts of a skin gland, and tumors of skin glands. Thus, the methods and apparatuses described herein may be used to for cosmetic treatments, including but not limited to one or more of: acne, oily skin, scar reduction or removal, sweat gland reduction or removal (hyperhidrosis), rosacea, rosacea-like dermatitis, xerosis cutis, asteatosis, seborrhea, seborrheic dermatitis, steatocystoma, bromhidrosis/osmidrosis, chromhidrosis, hidradenitis suppurativa, and/or Fox Fordyce disease.

Thus, described herein are cosmetic methods. For example, a cosmetic method of improving a skin appearance of a subject having a cosmetic flaw may include: positioning a plurality of electrodes so that a target gland in a region of a subject's skin is between two or more electrodes of the plurality of electrodes; applying pulsed electrical energy having a pulse duration in a sub-microsecond pulse range between the two or more electrodes of the plurality of electrodes at an energy density of less than $0.128 \text{ J/mm}^3$; and improving an appearance of the cosmetic flaw by eliminating or reducing the target gland without permanently damaging tissue outside the target gland.

In some variations a cosmetic method may improve a cosmetic flaw such as one or more of acne (including mild acne, moderate acne and/or severe acne), oily skin, body odor, and/or chromhidrosis.

The cosmetic methods described herein may include any of the method steps described herein. As described herein, in some variations the energy density is between $0.001 \text{ J/mm}^3$ and 0.08 J/mm³ for the plurality of electrodes, wherein the electrodes are arranged in an array having an area of between 2.25 mm² and 100 mm².

For example, a cosmetic method may include a cosmetic method of improving skin appearance of a subject having acne by selectively eliminating one or more glands within a region of skin. This method may include: placing one or more glands within a subject's skin between two or more electrodes of a plurality of electrodes; and applying pulsed electrical energy between the two or more electrodes of the plurality of electrodes, wherein pulses of the pulsed electrical energy have a pulse duration of between 0.01 nanoseconds and 1000 nanoseconds and a peak field strength of at least 0.1 kV/cm, wherein the energy density of the applied pulsed electrical energy is between about 0.001 J/mm³ and 0.080, thereby clearing the acne by elimination of the one or more glands without permanently damaging structures outside the target one or more glands.

As used herein treatment includes preventative treatment. Thus, when referring to "a method of treating a disorder", such as sebaceous hyperplasia, it is intended to cover and include a method of preventing such disorder.

Any of these methods may be methods of treating and/or preventing sebaceous hyperplasia (including cosmetic methods). For example, inserting the plurality of electrodes into the subject's skin may comprise inserting the plurality of electrodes into the subject's skin so that a sebaceous hyperplasia lesion within the subject's skin is between two or more of the plurality of electrodes.

In some variations the methods of treatment and/or prevention are used in conjunction with one or more pharmaceutical agents. The use of a pharmaceutical agent in conjunction with the pulsed electrical stimulation described herein may result in effects beyond what either treatment (e.g., pharmaceutical agent or pulsed electrical stimulation) alone may achieve. For example, any of these methods may include treating the skin with a pharmacological agent concurrently with applying the pulsed electrical energy. "Concurrently" in this context is intended to be broadly construed to include, actions that occur within a short period of time (for example, within few days) before or after, or on the same day as the application of the pulsed electrical energy. Examples of pharmacological agents include known dermatological agents, as well as antibiotics (e.g., erythromycin, clindamycin, cephalosporin, etc.), including antibacterial, antifungal, antiviral, etc.; steroids and steroid formulations (e.g., clioquinol, isoconazole, calcipotriol, fusidic acid, miconazole, salicylic acid, etc.), acne preparations, antihistamines, methotrexate, minoxidil, tetracycline, adapalene, isotretinoin, tretinoin, hydroquinone, isotretinoin, etc. The pharmacological agent may be taken orally and/or topically.

Any of the methods and apparatuses described herein may be used with (and/or may include) the use of a robotic system, e.g., for targeting and delivery of the therapy. For example, any of these methods may be computer-controlled or performed with a use of robotic system.

For example, a method of treating sebaceous hyperplasia may include: inserting a plurality of electrodes into a subject's skin so that a region of the subject's skin including a sebaceous gland is between two or more of the plurality of electrodes; and applying pulsed electrical energy between the two or more of the plurality of electrodes, wherein pulses of the pulsed electrical energy have a pulse duration of between 0.01 nanoseconds and 1000 nanoseconds, so that a total energy density delivered is equal or greater than a minimum treatment threshold sufficient to eliminate the sebaceous gland within the subject's skin without permanently damaging structures outside the target gland. As described above, the minimum treatment threshold may be 0.001 J/mm³, (e.g., 0.002 J/mm³, 0.003 J/mm³, 0.004 J/mm³, 0.005 J/mm³, 0.01 J/mm³, 0.02 J/mm³, 0.03 J/mm³, etc.) or less.

In any of the methods described herein, each needle electrode of the plurality of electrodes may be insulated. For example, any of these needle electrodes may include an insulated base portion and insulated tip portion.

Any of these methods may include inserting a pair of electrodes into the subject's skin before applying the plurality of high-field strength, short electrical pulses (e.g., pulses within the nanosecond range). For example, the electrodes may be inserted into the outer layers of skin to a depth of less than 5 mm, less than 4 mm, less than 3 mm, less than 2 mm, etc. The skin may be prepared ahead of time, e.g., washed, shaved, roughened, etc. Alternatively or additionally, the high-field strength, short (e.g., sub-microsecond) electrical pulses may be applied transdermally, without puncturing the skin. For example, any of these methods may include applying the set of electrodes on the surface of the subject's skin before applying the plurality of electrical pulses. In such variations one or more conductive or non-conductive gels or other materials may be applied to the skin, including to the electrode contact points and/or the region between them. For example, a non-conductive or lower-conductance gel may be used. Alternatively or additionally, a gel (low-conductance or non-conductive gels) may be used with needle electrodes.

While in some variations a pair of electrodes may be used, in other variations more than two electrodes (e.g., two or more active electrodes and two or more ground electrodes) may be used. The active electrodes may be coupled together; the ground electrodes may be coupled together.

As mentioned, applying the plurality of high-field strength, very short (e.g., nanosecond range) electrical pulses may include applying such pulses for less than a predetermined time (e.g., 1 second or less, 2 seconds or less, 5 seconds or less, 10 seconds or less, 15 seconds or less, 30 seconds or less, 45 seconds or less, 1 minute or less, 2 minutes or less, 3 minutes or less, 4 minutes or less, 5 minutes or less, 10 minutes or less, 15 minutes or less, etc.) and/or for a predetermined number of pulses (e.g., between 1 and 50 pulses, between 2 and 100 pulses, between 2 and 150 pulses, between 2 and 240 pulses, between 2 and 680 pulses, etc.). The pulses may be applied at any appropriate frequency. For example, the plurality of pulses may be applied between 0.05 Hz and 100 MHz (e.g., between about 1 Hz and 10 MHz, between 1 Hz and 50 MHz, between 1 Hz and 20 MHz, between 1 Hz and 10 MHz, between 1 Hz and 1 MHz, etc.).

Applying the plurality of high-field strength, very short (e.g., nanosecond) electrical pulses may increase a marker of inflammation within the region of the skin by less than a predetermined amount (e.g., less than 5%, less than 10%, less than 15%, etc.), wherein the marker of inflammation is one or of more of: leukocyte density, Interleukin-6, Interleukin-8, Interleukin-18, Tumor necrosis factor-alpha, and C-reactive protein. In particular, the marker may be an acute inflammatory marker, such as (but not limited to) leukocyte density.

In general, the electrical energy applied to the skin region may be in the form of one or more electrical pulses. The pulse duration may be at least 0.01 nanoseconds (ns). The pulse duration may also be at least 1 ns, or the pulse duration may be at least 5 ns. The pulse duration may be 1,000 ns or shorter. The duration of the pulse may also be in the range of 1 ns to 600 ns (e.g., 10 ns to 500 ns, 10 ns to 400 ns, etc.). Although pulses having nanosecond duration are described in the examples herein, in some implementations, the duration of the pulses may be in a picosecond ranges, or microsecond ranges, just to name a few.

The electrical field produced by each pulse may be at least 0.1 kV/cm (e.g., 1 kV/cm, etc.) at the peak amplitude of the pulse. The electrical field produced by each pulse may also be at least 10 kV/cm at the peak amplitude of the pulse. The electrical field produced by each pulse may be in the range of 1 kV/cm to 1,000 kV/cm at the peak amplitude of the pulse (e.g., the electrical field produced by each pulse may be in the range of 10 kV/cm to 100 kV/cm, 15 kV/cm to 50 kV/cm, 20 kV/cm to 30 kV/cm, etc.).

As mentioned, the number of electrical pulses during a single treatment may be at least 1. The number of pulses may also be at least 100. The number of pulses may be at least 1,000. The number of pulses may be less than 10,000. For example, the number of pulses may be between 20 and 200, between 30 and 150, between 30 and 100, etc. Pulses may be applied at a frequency of between 1 and 100 Hz, e.g., between 1 and 50 Hz, between 1 and 25 Hz, between 1 and 20 Hz, between 1 and 10 Hz, between 2 and 6 Hz, etc. The treatment time per session may be between 1 second and 60 seconds, between 5 seconds and 30 seconds, between 5 seconds and 20 seconds, etc.

The treatment may be an in vivo treatment of a skin region of a subject/patient (e.g., a human or animal subject or, equivalently, patient) comprising at least one treatment session, i.e. administration of the electrical energy to the skin by physician at an office visit. The treatment may also comprise a plurality of treatment sessions. For example, it may comprise at least two treatment sessions or at least three treatment sessions. In some implementation the target gland may be only partially eliminated or shrunk during the first treatment session, so the follow-up one or more sessions may be necessary to fully eliminate such gland.

For example, a method may include: inserting a plurality of electrodes into a region of a subject's skin between 2 and 5 mm deep, so that a region of skin including a target gland is between two or more of the plurality of electrodes, wherein each electrode comprises an uninsulated tip portion, and an insulated base portion extending between 0.1 mm and 1 mm from a base of the electrode; and applying pulsed electrical energy having a pulse duration in sub-microsecond pulse range between the two or more of the plurality of electrodes, wherein the pulsed electrical energy provides an energy density sufficient to eliminate the target gland without permanently damaging structures outside the target gland.

The energy density applied to the region of skin may be between about 0.001 J/mm$^3$ and about 0.008 J/mm$^3$ for an array of electrodes forming a pattern having an area of between 2.25 mm$^2$ and 100 mm$^2$. The region of the subject's skin may comprise a sebaceous hyperplasia lesion and wherein inserting the plurality of electrodes into the subject's skin comprises inserting the plurality of electrodes into the subject's skin so that the sebaceous hyperplasia lesion within the subject's skin is between two or more of the plurality of electrodes.

A method (e.g., a method of treating sebaceous hyperplasia) may include: positioning a plurality of electrodes such that a region of the subject's skin including a sebaceous gland is between two or more of the plurality of electrodes; and applying pulsed electrical energy between the two or more electrodes of the plurality of electrodes, wherein pulses of the pulsed electrical energy have a pulse duration of between 0.01 nanoseconds and 1000 nanoseconds, so that a total energy density delivered is within a treatment dose range of energy sufficient to eliminate the sebaceous gland within the subject's skin without permanently damaging structures outside the target gland.

Also described herein are systems configured to perform the methods described herein. For example, a system may include: a pulse generator configured to generate a plurality of electrical pulses having amplitude of at least 0.1 kV and a duration of less than 1000 nanoseconds; an applicator comprising a treatment tip having a plurality of needle electrodes, wherein each of the plurality of needle electrodes comprises: an insulated portion that extends anywhere from about 0.1 mm to about 1 mm from a base of the applicator, and an un-insulated portion extending from the end of the insulated portion to the distal end of each electrode; and a controller configured to apply a minimum treatment dose from the plurality of electrical pulses from the needle electrodes of the applicator, wherein the minimum dose provides an energy density sufficient to eliminate (e.g., in one or more sessions) the target gland without permanently damaging structures outside the target gland. In general, the system may be configured as a system for eliminating or reducing the number of glands in a subject's skin.

The system for treating tissue may be a system for treating a skin disorder. Thus, the system used for the treatment of the skin may include an applicator tip that comprises at least one delivery electrode and at least one ground electrode. Alternatively, a systems for treating tissue may be a system for cosmetically treating a subject. The applicator (e.g., applicator tip) may be any of the applicator tips described herein, including arrays of electrodes and/or applicator tips having a pattern of electrodes that may be rotated.

The pulse generator may be configured to provide pulses (including but not limited to nanosecond pulses) to be delivered by the applicator. The pulse generator and/or tip may be controlled by the controller. The controller may include one or more processors that may be configured to perform any of the treatment methods described herein. The one or more processors may be incorporated into the controller or may be a separate part. The controller and/or processor may include one or more memories, datastores, or the like that may be operationally connected to the processor(s).

The set of instructions executable by the processor(s) or the controller may be configured to perform any of the methods described herein. For example, the set of instructions may be configured to apply the pulsed electrical treatment to eliminate (e.g., in some variations by denucleating) the glands within the tissue (e.g., skin tissue). Thus, the set of instructions may control the timing (frequency, rate, duty cycle, etc.) of the applied electrical stimulation and/or the contact with the tissue, as well as pulse width and amplitude.

The apparatuses (e.g., systems) described herein may be configured to limit the energy or energy density applied in order to prevent undesired side effects, such as hyperpigmentation and/or volume loss of the treated tissue. In any of the variations described herein the controller may be configured to limit the energy density applied so that the likelihood of hyperpigmentation is 40% or less (35% or less, 30% or less, 25% or less, 20% or less, 15% or less, 10% or less, 5% or less, etc.) and/or the risk of volume loss is 10% or less (e.g., 9% or less, 8% or less, 7% or less, 6% or less, 5% or less, 4% or less, 3% or less, etc.), while maintaining an efficacy of 70% or more (e.g., 75% or more, 80% or more, 85% or more, 90% or more, 95% or more, etc.). Thus, the energy density may be limited to 0.120 $J/mm^3$ or less (e.g., 0.112 $J/mm^3$ or less, 0.104 $J/mm^3$ or less, 0.096 $J/mm^3$ or less, 0.088 $J/mm^3$ or less, 0.080 $J/mm^3$ or less, 0.072 $J/mm^3$ or less, etc.). For example, the energy density may be limited to 0.100 $J/mm^3$ or less so that the likelihood of hyperpigmentation is less than 40%, the likelihood of volume loss is less than 10, and the efficacy is greater than 90%. In some cases, the reduction in the likelihood of hyperpigmentation and/or volume loss may include a reduction in the severity of hyperpigmentation and/or volume loss; thus, in cases in which the likelihood of hyperpigmentation is 20% or less, the extent of the hyperpigmentation may be much less severe in those treated tissue regions that do have detectable hyperpigmentation.

For example, a system may include: a pulse generator configured to generate electrical pulses having an amplitude of at least 0.1 kV and a duration of less than 1000 nanoseconds; an applicator comprising a treatment tip having a plurality of needle electrodes; and; a controller coupled to the pulse generator and configured to apply a treatment dose from the plurality of needle electrodes to eliminate or reduce a size of a target gland within a subject's skin, wherein the controller regulates the treatment dose to have a maximum energy density of 0.128 $J/mm^3$ or less.

A system may include: a pulse generator configured to generate electrical pulses having an amplitude of at least 0.1 kV and a duration of less than 1000 nanoseconds; an applicator comprising a treatment tip having a plurality of needle electrodes, wherein each needle electrode of the plurality of needle electrodes comprises: an insulated portion that extends greater than 0.1 mm from a base of the treatment tip, and an un-insulated portion extending from an end of the insulated portion to a distal end of each needle electrode; and a controller coupled to the pulse generator and configured to apply a treatment dose from the plurality of needle electrodes to eliminate a target gland within a subject's skin, wherein the controller regulates the treatment dose to have a maximum energy density of 0.128 $J/mm^3$ or less.

In any of the systems described herein, the plurality of needle electrodes may be arranged in an array having an area of between 2.25 $mm^2$ and 100 $mm^2$.

The controller may include a user interface that may provide the user with one or more choices for applying treatment energy. In some variations the choices provided may limit the energy density applied in order to prevent side effects such as hyperpigmentation and/or volume loss, as mentioned above. In some variations the choices provided for applying treatment may be based on the region of the body to be treated, such as the face, neck, hands, arms, legs, back, chest, buttocks, etc. If the region to be treated is normally visible, and in particular corresponds to the face, the choices for treatment parameters may be adjusted to apply lower energy density and/or for reducing the likelihood of side effects such as hyperpigmentation and volume loss as just described; In contrast, where the region to be treated is not typically visible (e.g. non-facial regions) high energy density choices may be allowed or suggested. Although higher energy-density treatments may have a higher likelihood of side effects, the efficacy may be greater, requiring fewer re-treatments.

In some variations the methods and apparatuses described herein may be used to eliminate or modify hair follicles. For example, in some variations the methods described herein may be used to eliminate a hair follicle (e.g., for epilation). For example, the methods and apparatuses described herein may be used to apply pulsed electrical energy having a pulse duration in sub-microsecond pulse range between a plurality of electrodes, wherein the pulsed electrical energy provides an energy density sufficient to eliminate a hair follicle (or multiple hair follicles). The energy may be limited as described herein.

Also described herein are methods and apparatuses using a targeting aid (e.g., a targeting patch) for guiding or assisting in the treatment using any of the apparatuses and methods described. For example, a targeting patch device may include: an adhesive base formed of an electrically insulating material; a target region comprising a lip that is configured to receive a treatment tip of a therapeutic pulse generator to deliver pulses having an amplitude of at least 0.1 kV and a duration of less than 1000 nanoseconds from a plurality of needle electrodes; and wherein the target region comprises either: one or more openings through which the plurality of needle electrodes may extend to penetrate into a target tissue region when the patch is adhesively secured onto the target tissue, or a dielectric material configured to be penetrated by the plurality of needle electrodes may extend to penetrate into a target tissue region when the patch is worn on skin.

The adhesive base may be formed of silicone. In some variations this base is flat. In some variation, the adhesive base comprises a plurality of arms extending outward from the target region in a plane. The lip of the targeting region may extend partially or completely around the perimeter of the targeting region, for example, around the opening(s) of the target region or around the dielectric material configured to be penetrated. In variations for use with a retractable housing, the lip may extend across the targeting region (or partially across) to help retract a retractable housing covering the electrode(s). The target region may be located centrally relative to the base.

In some variations, the targeting patch includes one or more fiducial marks configured to guide insertion of the treatment tip into the target region. The one or more fiducial marks may be centered around the target region. The one or more fiducial marks may be one or more of: raised from the surface of the base; colored, sunken into the base, a plurality of lines oriented to converge at a center of the target region.

In use, the targeting patch may guide the applicator tip of an apparatus for applying pulsed electrical energy to target a tissue. For example, a method of applying pulsed electrical energy may include: securing a targeting patch device to a subject's tissue over a target tissue region; engaging a treatment tip of a therapeutic pulse generator to a target region of the targeting patch device and penetrating a dielectric material within the target region of the targeting patch device so that a plurality of needle electrode extends through the target region and into the target tissue; and applying pulsed electrical energy from the needle electrodes into the target tissue.

A method of applying pulsed electrical energy, the method comprising: securing a targeting patch device to a subject's tissue over a target tissue region; engaging a treatment tip of a therapeutic pulse generator to a target region of the targeting patch device and penetrating the target tissue with a plurality of needle electrodes through the target region of the targeting patch device; and applying pulsed electrical energy from the needle electrodes into the target tissue. Any of these methods may include adhesively securing the targeting patch to the tissue (e.g., skin).

Other and further features and advantages of the present disclosure will become apparent from the following detailed description when read in view of the accompanying figures.

BRIEF DESCRIPTION OF THE DRAWINGS

The novel features of the apparatuses and methods described herein are set forth with particularity in the claims that follow. A better understanding of the features and advantages of these apparatuses and methods will be obtained by reference to the following detailed description that sets forth illustrative embodiments, in which the principles of the invention are utilized, and the accompanying drawings of which:

FIG. 4 is a section through the treated region of skin, showing full recovery and a substantial loss in dermal glands in the treatment area. Scale bar on bottom left is 1 mm.

FIG. 5 is a section through both treated and adjacent skin. The scale bar on the bottom left is 1 mm. Black ovals indicate the locations of sebaceous glands in both the treated and untreated skin regions.

FIG. 6A shows the skin prior to treatment ("baseline"). FIG. 6B shows the same region of skin immediately after treatment. FIG. 6C shows the same region of skin 7 days after treatment, showing a crust of tissue over the treated region. By 30 days after treatment, shown in FIG. 6D, the skin has recovered, showing exposed new epidermis that appears nearly identical to the nearby untreated normal skin, and the SH lesion has been cleared.

FIG. 7A shows the skin prior to treatment ("baseline"). FIG. 7B shows the same region of skin immediately after treatment. FIG. 7C shows the same region of skin 7 days after treatment, showing a crust of tissue over the treated region. By 30 days after treatment, shown in FIG. 7D, the skin has recovered, showing exposed new epidermis that appears nearly identical to the nearby untreated normal skin, and the SH lesion has been cleared.

FIG. 8A shows the skin prior to treatment ("baseline"). FIG. 8B shows the same region of skin immediately after treatment. FIG. 8C shows the same region of skin 8 days after treatment, showing a crust of tissue over the treated region. By 30 days after treatment, shown in FIG. 8D, the skin has recovered, showing exposed new epidermis that appears nearly identical to the nearby untreated normal skin, and the SH lesion has been cleared.

FIG. 9A shows the skin prior to treatment ("baseline"). FIG. 9B shows the same region of skin immediately after treatment. FIG. 9C shows the same region of skin 9 days after treatment, showing a crust of tissue over the treated region. By 30 days after treatment, shown in FIG. 9D, the skin has recovered, showing exposed new epidermis that appears nearly identical to the nearby untreated normal skin, and the SH lesion has been cleared.

FIG. 10A shows the skin prior to treatment ("baseline"). FIG. 10B shows the same region of skin immediately after treatment. FIG. 10C shows the same region of skin 10 days after treatment, showing a crust of tissue over the treated region. By 30 days after treatment, shown in FIG. 10D, the skin has recovered, showing exposed new epidermis that appears nearly identical to the nearby untreated normal skin, and the SH lesion has been cleared.

FIG. 11A shows the skin prior to treatment ("baseline"). FIG. 11B shows the same region of skin immediately after treatment. FIG. 11C shows the same region of skin 11 days after treatment, showing a crust of tissue over the treated region. By 30 days after treatment, shown in FIG. 11D, the skin has recovered, showing exposed new epidermis that appears nearly identical to the nearby untreated normal skin, and the SH lesion has been cleared.

FIGS. 12A-12D illustrate an example of an applicator hand piece (FIG. 12A) and examples of various electrode tips (FIGS. 12B-12D) for an apparatus for treating skin by delivering electrical pulses as described herein. The tips shown in FIGS. 12B-12D may be attached to the end of the applicator of FIG. 12A. FIGS. 12B and 12C show needle electrodes, while FIG. 12D shows an example of a non-penetrating (plate) electrode. The hand piece shown in FIG. 12A may plug into a generator.

FIG. 13 is an example of another applicator tip with one delivery electrode and four ground electrodes.

FIG. 14A is a front view. FIG. 14B is a top view. FIG. 14C is an enlarged view of the electrodes on the tip. FIG. 14D is a perspective view. FIG. 14E is a side view and FIG. 14F is an enlarged side view of the electrodes on the tip.

FIG. 15A is a front perspective view, while FIG. 15B is a slightly enlarged view of the needle electrodes on the tip.

In FIGS. 16A and 16B, the tip includes a set of fiducials (arranged as a cross) centered on the electrodes. FIG. 16A is a front perspective view, while FIG. 16B is a slightly enlarged view of the electrodes and the set of fiducials.

FIG. 17A shows a pair of needle electrodes extending from an insulated base. FIG. 17B shows a similar pair of needle electrodes having an insulated region of the electrode length near the base of the electrode tip. FIG. 17C shows another pair of needle electrodes, similar to that shown in FIG. 17A, with a longer length of insulated region (approximately half of the length). FIG. 17D shows another pair of needle electrodes with the majority of the length insulated, except for the distal tip.

FIG. 18A shows an example of an applicator tip, showing the distal end face of the retractable treatment applicator tip in which the treatment needle electrodes are fully enclosed in a retractable electrode housing.

FIG. 18B shows the retractable applicator tip device of FIG. 18A with a force sufficient to overcome the bias holding the electrode housing portion of the retractable applicator tip housing distally, exposing the treatment needle electrodes.

FIGS. 28A is an image of a patient's face immediately (30 seconds) after treatment; FIG. 28B is a thermographic image of the same region of the patient's face. FIG. 28C shows another image of the patient's face 30 seconds after treatment; FIG. 28D is a thermographic image of the same region of the patient's face shown in FIG. 28C.

DETAILED DESCRIPTION

Figure 1:
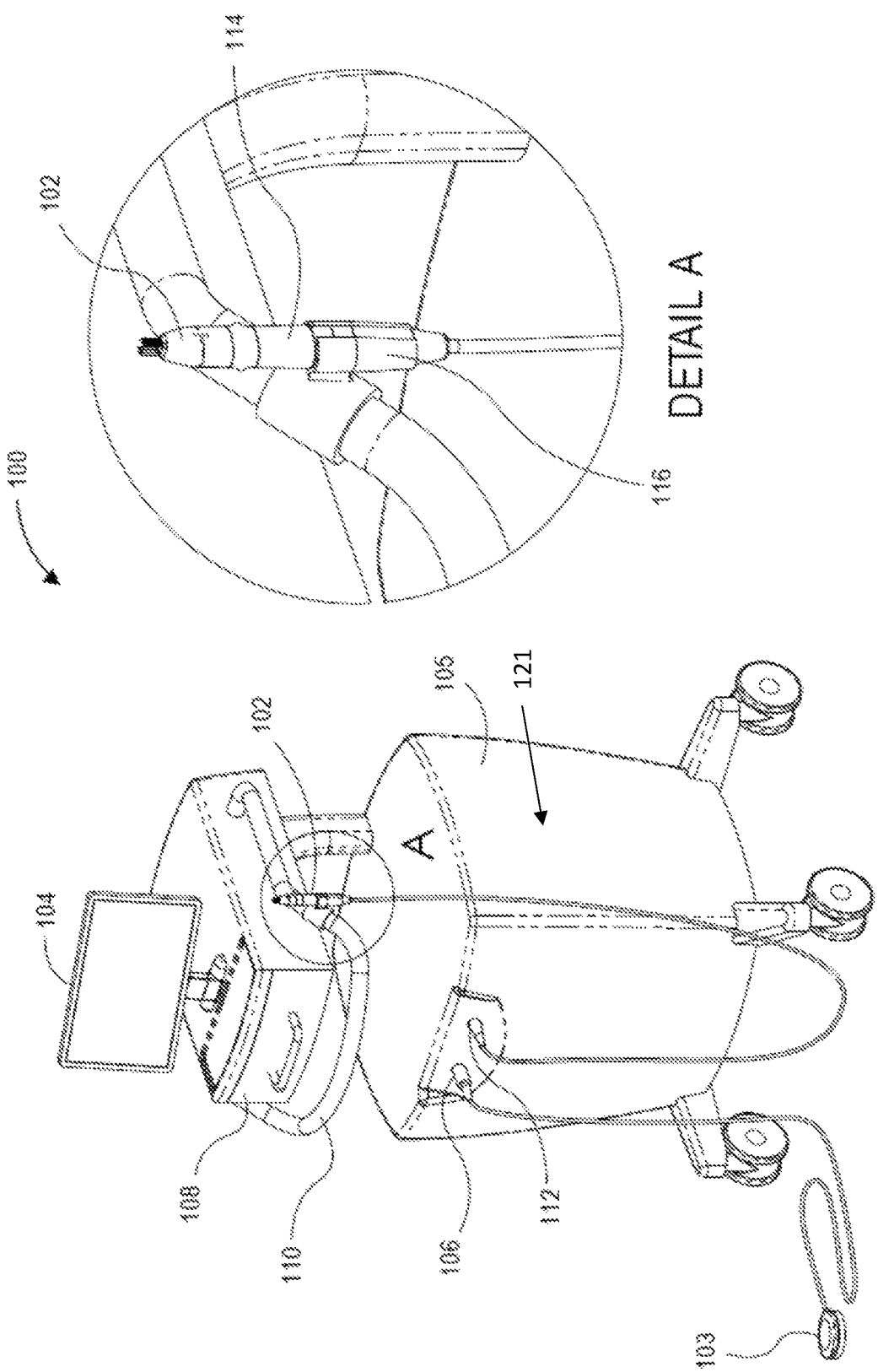
FIG. 1 is an example of a system for generation and delivering electrical pulses, e.g., pulses in the nanosecond range.

In general, described herein are methods and apparatuses for treating skin tissue to eliminate all or some of the glands (e.g., sebaceous, eccrine, apocrine) within the targeted region of the tissue by applying pulsed (e.g., very short pulses) electric treatment to the target region of the tissue. Any of the methods described herein may be used to treat and/or prevent a disorder associated with a skin gland. Also described herein are cosmetic treatments associated with a skin gland. For example, the methods and apparatuses (e.g., systems and devices) described herein may be used to treat and/or prevent sebaceous hyperplasia, acne, syringoma, and/or rosacea, just to name a few.

Although the examples described herein illustrate primarily the treatment to eliminate (e.g., reduce the number of) sebaceous glands within a target region of skin tissue, other skin glands may also be treated in essentially the same manner described herein. The methods and apparatuses described herein may be used to eliminate any gland within (e.g., deep within) the dermis. For example, eccrine glands are sweat glands that are not connected to hair follicles. They function by responding to elevated body temperature due to the environmental heat or physical exercise. They produce sweat that contains electrolytes and water, which cools the body when it evaporates from the skin. Eccrine glands occur over most of the body and open directly onto the surface of the skin. These glands are common on the forehead, neck and back. They are also responsible for the moisture that may appear on the palms and soles when a person is emotionally stressed. Apocrine glands are a subtype of exocrine secretory glands. They are found in many locations but are primarily in the axillae, areolae, and anogenital region. While in the past, certain glands, such as those in the areolae, were considered modified apocrine glands, it is now recognized that all of these glands are true apocrine glands. Apocrine glands release their products by "decapitation," a process by which membrane-bound cytoplasm from the apical surface of the cells buds off into the lumen of the duct and is secreted. Apocrine glands are associated with multiple pathologies, including apocrine bromhidrosis, apocrine chromhidrosis, apocrine carcinoma of the breast, Fox- Fordyce disease, and hidradenitis suppurativa (acne inversa). The skin glands may extend between 1 mm and 5 mm deep into the skin.

The methods and apparatuses described herein may be used to treat skin tissue by generally applying a treatment, e.g., a pulsed electrical treatment, to the skin to specifically eliminate all or some of the glands within a treatment zone (e.g. target region) of the skin. Without being bound by a particular theory of operation, the glands may be eliminated by destroying the nuclei (e.g., de-nucleating) of the cells of the gland. Other methods of making the gland cells within the target skin region non-viable may occur, including disrupting or destroying other organelles in the cells, such as the endoplasmic reticulum, mitochondria, etc., or by disrupting the outermost cell membrane (e.g. plasma membrane). The non-thermal treatment employed in the methodology of the present disclosure is typically electric treatment (e.g., very short, high-field strength electric pulses, typically in the sub-microsecond range) adapted to de-nucleate gland cells. These pulses may affect the gland cells without provoking an inflammatory response (e.g., without increasing the density of leukocytes and/or melanocytes above a threshold percentage compared to untreated skin). The methods and apparatuses described herein may selectively eliminate the glands (e.g., sebaceous glands) in the tissue without irrevocably destroying the overlying and/or adjacent tissue, including the epidermis and dermis. The destruction of the glands may refer to the entire gland, including portions extending out of the target treated tissue, and destruction may refer to the fact that the glands, unlike the adjacent tissues, may not recover within a recovery period (e.g., 1 week, one month, two months, three months, etc.). Sometimes, more than one treatment may be required to completely eliminate the entire gland.

Illustrative embodiments are now discussed. Other embodiments may be used in addition or instead. Details which may be apparent or unnecessary may be omitted to save space or for a more effective presentation. Conversely, some embodiments may be practiced without all of the details which are disclosed.

In any of the methods described herein, the pulsed electrical treatment may be nanosecond electric pulsed treatment, which may include the application of electrical pulses with duration of 1,000 nanoseconds (ns) or less. Although the examples described herein focus primarily on pulses having a width (pulse width) within the nanosecond range, other pulse widths may be used. For example, in some variations, pulses may have pulse widths in picosecond ranges, microsecond ranges, or millisecond ranges, just to name a few.

The pulsed electrical treatment, may be achieved by providing electrical energy to the target skin region in a form of one or more electrical pulses. During this treatment, tissue removal may not be intentional and, if it happens, may not be substantial. Thus, the treatment may thereby be advantageous over current or other proposed treatment techniques since it may achieve its purpose with no substantial tissue removal. Further, these methods may be generally non-thermal, and may be configured to prevent a substantial inflammatory response.

Although in some variations, the treatment of the skin may result in the destruction of the gland, in some variations, treatment may reduce the volume of the skin gland. That is, the treatment may induce at least shrinkage of the skin gland. This shrinkage may be at least 10%, 20%, 30%, 60%, 70%, 80%, 90%, or more than 90% (up to and including complete removal). The treatment may reduce the skin gland volume to a negligible level (i.e., clearance). The skin gland growth prevention or the volume reduction may be achieved in at least 10%, 20%, 30%, 40%, 50%, 60%, 70%, 80%, 90%, or more than 90% of cases.

When the skin gland volume shrinks to a negligible size (i.e. about 100% shrinkage), the skin gland is "cleared". If the gland shrinkage is in the range of >10% and <50%, it is concluded that there is lesion "shrinkage". If the gland shrinkage is in the range of >50% and <100%, it is concluded that there is "substantial shrinkage".

The treatment may comprise at least one treatment session. For example, the treatment session may comprise an administration of the electrical energy to the skin region of a human by physician at an office visit. The treatment of a skin region may also comprise a plurality of treatments sessions. For example, it may comprise at least two treatment sessions or at least three treatment sessions. As mentioned above, if the gland shrinks only partially after the first treatment, one or more additional sessions may be required to achieve 100% shrinkage or elimination of the target gland. These treatments may be combined with any other type of treatments to increase efficacy of the treatment. These other treatments may include over-the-counter treatments, treatments with prescription medicines, surgery, and destructive procedures. For example, these other treatments may include curettage, electrodessication, cryotherapy, topical therapy, and combinations thereof.

Any system suitable for delivery of electrical pulses with the target energy level may be used. A pulse generator may be any pulse generator that is capable of generating pulses, for example, with a duration of 1,000 ns or less. The pulse delivery device may be any device that can deliver electrical pulses to the skin lesion. This device may have an applicator tip that may comprise at least one pair of delivery electrodes. In some embodiments, additional delivery electrodes may be electrically floating and may be switched to become active, as desired. This applicator may comprise at least one ground electrode. The delivery electrode and/or the ground electrode may penetrate into the skin lesion to deliver the electrical pulses to the target skin region including the gland(s) to be treated.

For example, a nanosecond pulse generator system such as those shown and described in US2017/0245928A1 (U.S. patent application Ser. No. 15/148,344, titled "HIGH-VOLTAGE ANALOG CIRCUIT PULSER WITH FEEDBACK CONTROL"), which is incorporated herein by reference in its entirety, may be used. The pulse generator system may provide pulses having a duration of 1,000 ns or less to the skin lesion. The system may comprise a power supply, a controller, a pulse generator, and a pulse delivery device (e.g., a wand, or treatment applicator). An example of this system is schematically shown in FIG. 1. FIG. 1 illustrates one example of a nanosecond pulse generator system (NsPEF system). The pulse generator system 100 includes electrode 102, footswitch 103, and interface 104. Footswitch 103 is connected to housing 105 and the electronic components therein through connector 106. Electrode (e.g., treatment tip 102) in this example is connected to housing 105 and the electronic components therein through high voltage connector 112. NsPEF system 100 also includes a handle 110 and storage drawer 108. As shown in DETAIL A portion of FIG. 1, nsPEF system 100 also includes holster 116, which is configured to hold electrode 102 at its handle portion 114.

A human operator may input a number of pulses, amplitude, pulse duration, and frequency information, for example, into a numeric keypad or a touch screen of interface 104, and/or some or all of these parameters may be automatically determined based on a target treatment protocol, such as a gland treatment protocol. In some embodiments, the pulse width can be varied. A microcontroller sends signals to pulse control elements within nsPEF system 100. In some embodiments, fiber optic cables allow control signaling while also electrically isolating the contents of the metal cabinet with nsPEF generation system 100, the high voltage circuit, from the outside. In order to further isolate the system, system 100 may be battery powered instead of from a wall outlet.

The applicator may include or be coupled to a treatment tip 102 having two or more (e.g., a plurality) of electrodes. The system may generally include a controller 121. The controller may control operation of the system, and may include one or more processors, one or more memories, and the like. The controller may include logic (e.g., hardware, software, firmware) including instructions that, when executed by the one or more processor(s), may control the system to apply the electrical therapy as described herein. For example, the set of instructions may operate a robotic actuator (e.g., robotic arm) to move the treatment electrodes to the target tissue region and/or control the application of pulsed electrical energy treatment to the tissue. The set of instructions may include instructions controlling the application of the pulses, rotation of the pattern of electrodes applying the energy, and/or placement of the applicator on/off of the tissue. In some variations, the applicator may control the application of pulsed electrical energy to cause the elimination (e.g., de-nucleation) of cells of the glands within the target skin tissue (e.g., sebaceous glands, eccrine glands, or apocrine glands).

The electrical energy may be applied to the skin lesion in the form of at least one electrical pulse. For example, between 1 and 10000 pulses may be applied (e.g., between 30 and 1000). In one embodiment, at least 10 pulses, at least 100 pulses, at least 1000 pulses, or at least 2000 pulses may be applied to treat the skin during a single treatment. The duration of one or more of the pulses may be in the range of 0.01 ns to 1,000 ns. For example, the pulse width may be between 50 and 500 ns (e.g., between 200 and 300 ns). The duration of one or more of the pulses may be, for example, in sub-microsecond range.

The total estimated energy density applied per volume of the skin being treated may be at least 0.01 $J/mm^3$ (e.g., at least 0.02 $J/mm^3$, at least 0.03 $J/mm^3$, at least 0.04 $J/mm^3$, at least 0.05 $J/mm^3$, at least 0.06 $J/mm^3$, at least 0.07 $J/mm^3$, etc.). Although this range of energy densities may have a high efficacy in treating glands as described herein, in some variations, the total estimated energy density applied per volume of the skin being treated may be lower. For example, the total estimated energy densities applied may be between 0.001 $J/mm^3$ and 0.350 $J/mm^3$ (e.g., between about 0.001 $J/mm^3$ and about 0.3 $J/mm^3$, between about 0.001 $J/mm^3$ and about 0.2 $J/mm^3$, between about 0.001 $J/mm^3$ and 0.15 $J/mm^3$, between about 0.001 $J/mm^3$ and about 0.125 $J/mm^3$, between about 0.001 $J/mm^3$ and about 0.115 $J/mm^3$, between about 0.001 $J/mm^3$ and about 0.11 $J/mm^3$, between about 0.001 $J/mm^3$ and about 0.1 $J/mm^3$, etc.). In some variations the energy applied may be limited to prevent side effects such as hyperpigmentation and/or volume loss, while maintaining efficacy above a threshold (e.g., 80% or more, 85% or more, 90% or more 95% or more, etc.). For example, in some variation the energy applied by the applicator may be 3 J or less, 2.5 J or less, 2 J or less, 1.75 J or less, 1.5 J or less, 1.25 J or less, 1.0 J or less, 0.7 J or less, 0.5 J, 0.4 J or less, etc., e.g., when using an applicator having an array of electrodes forming a pattern having a width and a height of between 1.4 mm and 5.5 mm. For example, for an applicator delivering energy in a 2.5 mm×2.5 mm×2 mm volume, the delivered energy may be about 0.24 $J/mm^3$ or less, about 0.2 $J/mm^3$ or less, about 0.16 $J/mm^3$ or less, about 0.14 $J/mm^3$ or less, about 0.12 $J/mm^3$ or less, about 0.112 $J/mm^3$ or less, about 0.104 $J/mm^3$ or less, about 0.096 $J/mm^3$ or less, about 0.088 $J/mm^3$ or less, about 0.08 $J/mm^3$ or less, about 0.072 $J/mm^3$ or less, etc. Lower energy densities may reduce the amount of hyperpigmentation and volume loss while still achieving an acceptable efficacy.

In some variations, the energy applied may be at least 0.001 $J/mm^3$ (e.g., at least 0.005 $J/mm^3$, at least 0.008 $J/mm^3$, at least 0.010 $J/mm^3$, at least 0.020 $J/mm^3$, at least 0.030 $J/mm^3$, at least 0.040 $J/mm^3$, etc.). In another embodiment, the total applied electrical energy per volume of the treated skin may be in the range of, e.g., between about 0.001 $J/mm^3$ and about 0.120 $J/mm^3$ (e.g., between about 0.008 $J/mm^3$ and about 0.120 $J/mm^3$, between about 0.016 $J/mm^3$ and about 0.112 $J/mm^3$, between about 0.016 $J/mm^3$ and about 0.104 $J/mm^3$, between about 0.016 $J/mm^3$ and about 0.096 $J/mm^3$, etc.).

The electrical field produced by each pulse may be at least 0.1 kV/cm (e.g., at least 1 kV/cm, etc.) at the peak amplitude of the pulse. For example, the applied electrical field may be between 1 and 50 kV/cm (e.g., between 10 to 30 kV/cm). In another embodiment, the electrical field produced by each pulse may be in the range of 0.1 kV/cm to 1,000 kV/cm (e.g., between 0.1 kV/cm and about 100 kV/cm, etc.) at the peak amplitude of the pulse. Yet, in another embodiment, the electrical field produced by each pulse may be in the range of 1 kV/cm to 100 kV/cm at the peak amplitude of the pulse.

The treatment may comprise at least one treatment session, i.e. administration of the electrical energy to the target skin region by physician at an office visit. This treatment session may comprise at least one application of the electric energy to the target skin region. The electrical energy may be delivered to the skin in any manner suitable for the target skin region. For example, the electrical energy may be delivered after penetrating the target skin region by electrodes of the applicator tip. The electric energy may be delivered after insertion of the electrodes into the skin. For example, one application may comprise first penetration of the target skin region by the electrodes of the applicator tip and then delivery of a desirable number of pulses, for example, between 30-1000 pulses, with a pulse duration of between about 100 to 600 ns. More than one application may be used per treatment session to treat the target skin region. The number of applications may depend on the size of the target skin region. Larger regions may require more than one application per treatment session, as discussed in detail below. The treatment of the target skin region may also comprise a plurality of treatment sessions. For example, it may comprise at least two treatment sessions or at least three treatment sessions. These treatment sessions may also be separated in time by 1 or more days (e.g., 2 days, 3 days, 4 days, 5 days, 6 days, 7 days, etc.).

Although many of the variations described herein refer to the insertion of tissue-penetrating electrodes, such as needle electrodes, into the skin, any appropriate electrode may be used. For example plate electrodes may be used. Tissue including one or more skin glands may be placed between two plate electrodes. In some variations non-penetrating electrodes, including surface electrodes, may be used.

Figure 2A:
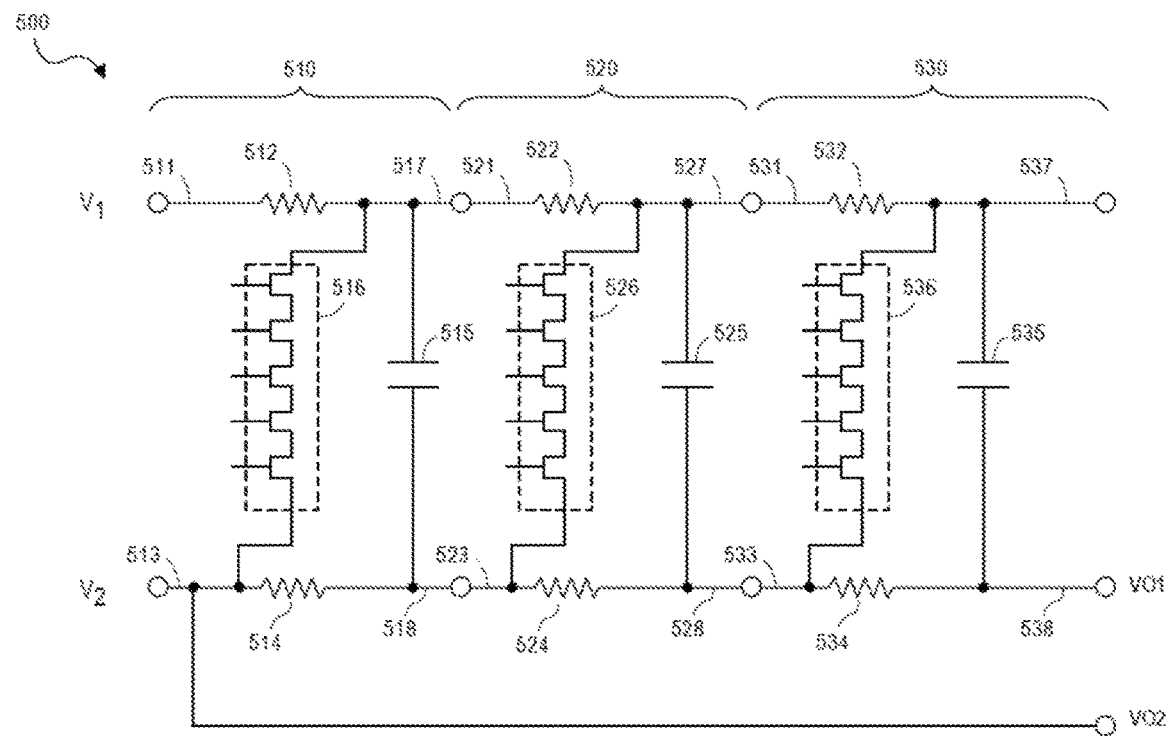
FIG. 2A is an electrical schematic of one example of a pulse generator.
Figure 2B:
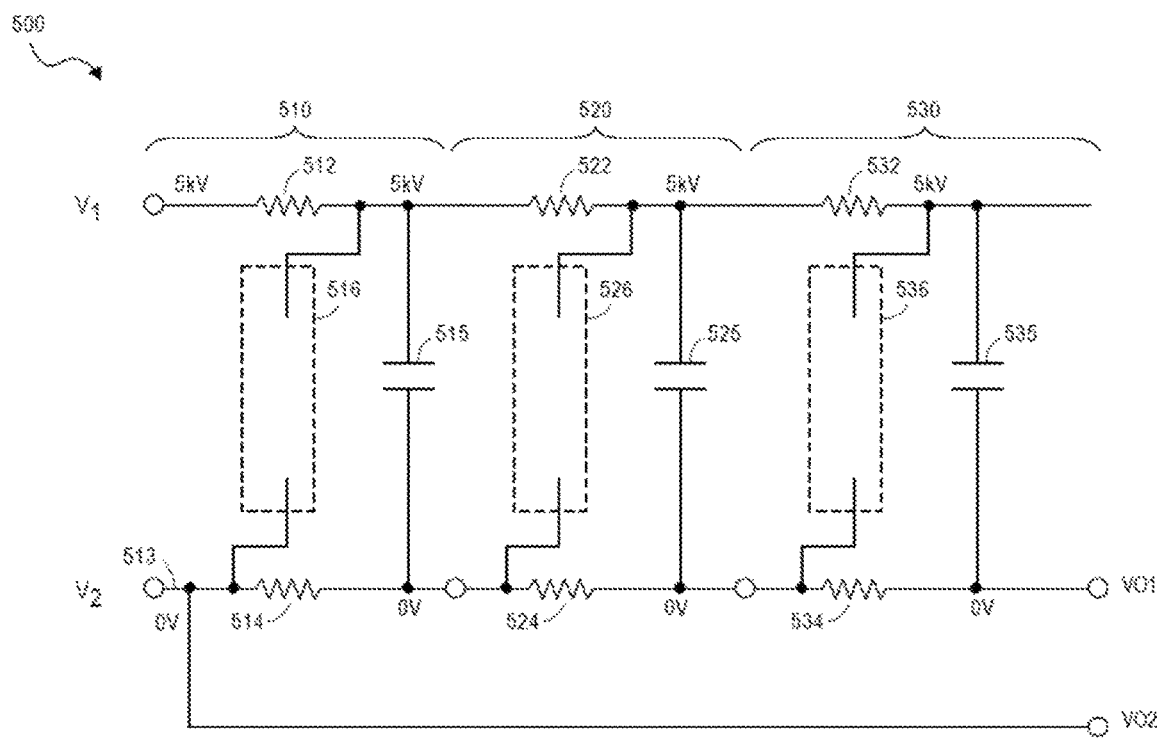
FIG. 2B schematically illustrates the pulse generator of FIG. 2A during a charge mode.
Figure 2C:
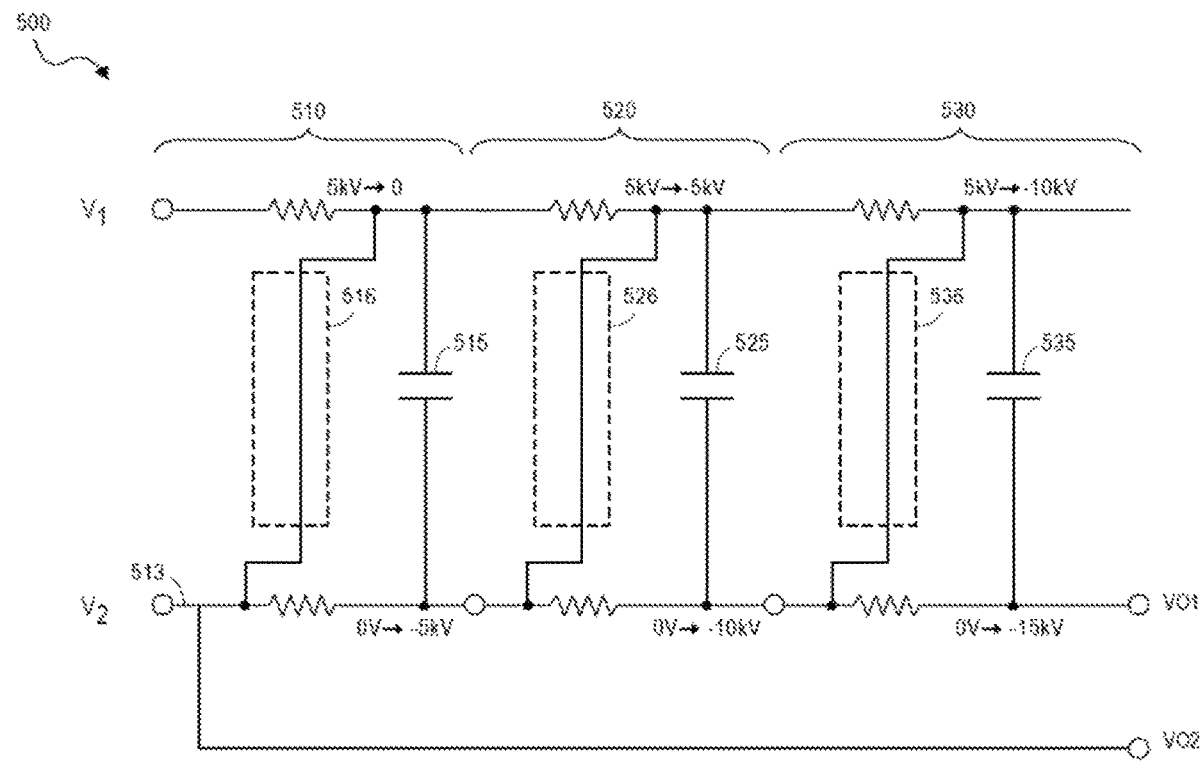
FIG. 2C schematically illustrates the pulse generator of FIG. 2A during a discharge mode.

As stated above, an electrical pulse generation and delivery system is schematically shown in FIG. 1 and includes a pulse generator. An example of the pulse generator is schematically shown in FIGS. 2A-2C. FIG. 2A illustrates a pulse generator circuit 500 which may be used inside nsPEF system 100 such as the one shown in FIG. 1. Pulse generator circuit 500 may illustrate a panel comprising a Marx generator switched by three switch stacks. This example of a nsPEF system can have a single pulse generator circuit panel. In some embodiments, a nsPEF system includes multiple panels in parallel.

Circuit 500 includes three stages, 510, 520, and 530. In some embodiments, another number of stages is used. For example, in some embodiments, 2, 4, 5, 6, 7, 8, 9, or 10 stages are used. Stage 510 includes resistors 512 and 514, capacitor 515, and switch stack 516. Likewise, stage 520 includes resistors 522 and 524, capacitor 525, and switch stack 526, and stage 530 includes resistors 532 and 534, capacitor 535, and switch stack 536. Each of these elements have structure and functionality which is similar to the corresponding elements of stage 510.

Stage 510 has first and second voltage input terminals 511 and 513 and first and second voltage output terminals 517 and 518. Stage 520 has first and second voltage input terminals 521 and 523, and first and second voltage output terminals 527 and 528. Stage 530 has first and second voltage input terminals 531 and 533, and first and second voltage output terminals 537 and 538.

The first and second voltage input terminals 511 and 513 of stage 510 are respectively connected to first and second power supply input terminals $V_1$ and $V_2$. The first and second voltage output terminals 517 and 518 of stage 510 are respectively connected to the first and second voltage input terminals 521 and 523 of stage 520. The first and second voltage output terminals 527 and 528 of stage 520 are respectively connected to the first and second voltage input terminals 531 and 533 of stage 530. The second voltage output terminal 538 of stage 530 and second voltage input terminal 513 of stage 510 are respectively connected to first and second power output terminals VO1 and VO2.

The exemplary pulse generator circuit 500 shown in FIG. 2A operates in a charge mode and in a discharge mode. During the charge mode, described below with reference to FIG. 2B in more detail, capacitors 515, 525, and 535 are charged by current received from the first and second power supply input terminals $V_1$ and $V_2$. During the discharge mode, described below with reference to FIG. 2C in more detail, capacitors 515, 525, and 535 are discharged to provide a current to a load (not shown) connected across first and second power output terminals VO1 and VO2.

FIG. 2B illustrates pulse generator circuit 500 during charge mode. First and second input voltages are respectively applied to first and second power supply input terminals $V_1$ and $V_2$ while each of switch stacks 516, 526, and 536 are nonconductive or open, and while first and second power output terminals may be disconnected from the load (not shown). Because each of switch stacks 516, 526, and 536 are open, substantially no current flows therethrough, and they are represented as open circuits in FIG. 2B. During the charge mode, each of capacitors 515, 525, and 535 are charged by current flowing through resistors 512, 522, 532, 534, 524, and 514 to or toward a voltage equal to the difference between the first and second input voltages.

Each of the switches of switch stacks 516, 526, and 536 has a breakdown voltage rating which should not be exceeded. However, because the switches are serially connected, the capacitors 515, 525, and 535 may be charged to a voltage significantly greater than the breakdown voltage of the individual switches. For example, the breakdown voltage of the switches may be 1 kV, and the capacitors 515, 525, and 535 may be charged to a voltage of 5 kV, when 5 or more switches are used in each switch stack.

For example, the first and second input voltages may respectively be 5 kV and 0 V. In such an example, each of the capacitors 515, 525, and 535 is charged to or toward a voltage equal to 5 kV. In some embodiments, the difference between the first and second input voltages is limited to be less than 10 kV.

FIG. 2C illustrates pulse generator circuit 500 during discharge mode. First power supply input terminal $V_1$ may be disconnected from the first input voltage. In some embodiments, first power supply input terminal $V_1$ remains connected to the first input voltage. Second power supply input terminal $V_2$ remains connected to the second input voltage. In addition, each of switch stacks 516, 526, and 536 are conductive or closed. Because each of switch stacks 516, 526, and 536 are closed, current flows therethrough, and they are represented as conductive wires in FIG. 2C. As a result, a low impedance electrical path from power supply input terminal $V_2$ to power output terminal VO1 is formed by switch stack 516, capacitor 515, switch stack 526, capacitor 525, switch stack 536, and capacitor 535. Consequently, the difference between the voltages at the power output terminals VO1 and VO2 is equal to the number of stages (in this example, 3) times the difference between the first and second input voltages. Where the first and second input voltages are respectively 5 kV and 0 V, a voltage difference of 15 kV is developed across the power output terminals VO1 and VO2.

Other examples of pulse generators and systems that may be used with any of the methods of the present disclosure and/or may be modified to form any of the apparatuses described herein are shown and described in co-pending U.S. patent publication no. 20180078755, U.S. patent publication no. 20170326361, U.S. patent publication no. 20170246455, U.S. patent publication no. 201802433558, and U.S. patent publication no. 20170319851; each of these patent application is herein incorporated by reference in its entirety.

The electrical pulses may be delivered to a target skin region by using applicator tips comprising one or more delivery electrode(s) and at least one ground electrode. For example, needle electrodes may be constructed by using a 30 gauge needle (i.e. about 0.255 mm in diameter). The delivery and the ground electrodes may have the same length for each applicator tip. This length may be varied, for example, in the range of about 2 millimeters (mm) to 5 mm. The electrodes may be arranged to form an open pattern (in these examples, shown as a square pattern, though other shapes may be used). The needle electrodes may be embedded in an insulator (e.g., a Teflon insulation). Any appropriate, preferably biocompatible, electrical insulator may be used, such as, for example, polyvinyl chloride (PVC), polyethylene (PE), PEEK, polyimide, neoprene, rubber, thermoplastic elastomers, and/or conformal coatings like Parylene.

The tip configuration may vary, as will be described in FIGS. 12A-16B, below. There applicator tip configurations may be suitable for the treatment of the target skin region as described herein. These configurations may include tips comprising at least one delivery electrode and at least one ground electrode.

Each pulse may include a carrier frequency. For example, a pulse may contain significant frequency components centered at about 142.9 megahertz (MHz), and each pulse with a duration of about 14 ns contained significant frequency components centered at about 71.4 MHz. Electrical nanosecond pulses with different amplitudes (e.g., peak amplitude of about 7.0 kilovolts (kV), peak amplitude of about 5.5 kV, etc.) may be used.

Values of the pulse durations and the peak amplitudes referred to herein may be average values unless specifically noted. These pulse durations and the peak amplitudes may vary with a standard deviation of, e.g., 10% of their average values. In general, the skin impedance values may be related to the design of the electrode being used. The target skin region resistance may be expected to be, depending on the size of the target skin region and/or electrodes, and any insulation on the electrodes, between about 10 and greater than about 700 Ohms. For example, see the electrodes shown in FIGS. 14-16 and described in detail below. Different electrode designs may register different tissue impedances, e.g., between about 100 Ohms and 1 KOhm (e.g., from 150 Ohms to 800 Ohms), depending on the quality of the electrode contact, which may be (in part) a function of the electrode design.

A study was done on human subjects to evaluate treatment of skin to eliminate or reduce sebaceous glands in a target skin region using different treatment applicators (treatment tips), including 1.5 mm×1.5 mm, 2.5 mm×2.5 mm and 5 mm×5 mm tips (similar to those shown in FIGS. 14A to 16B and FIGS. 18A-18B).

Figure 4:
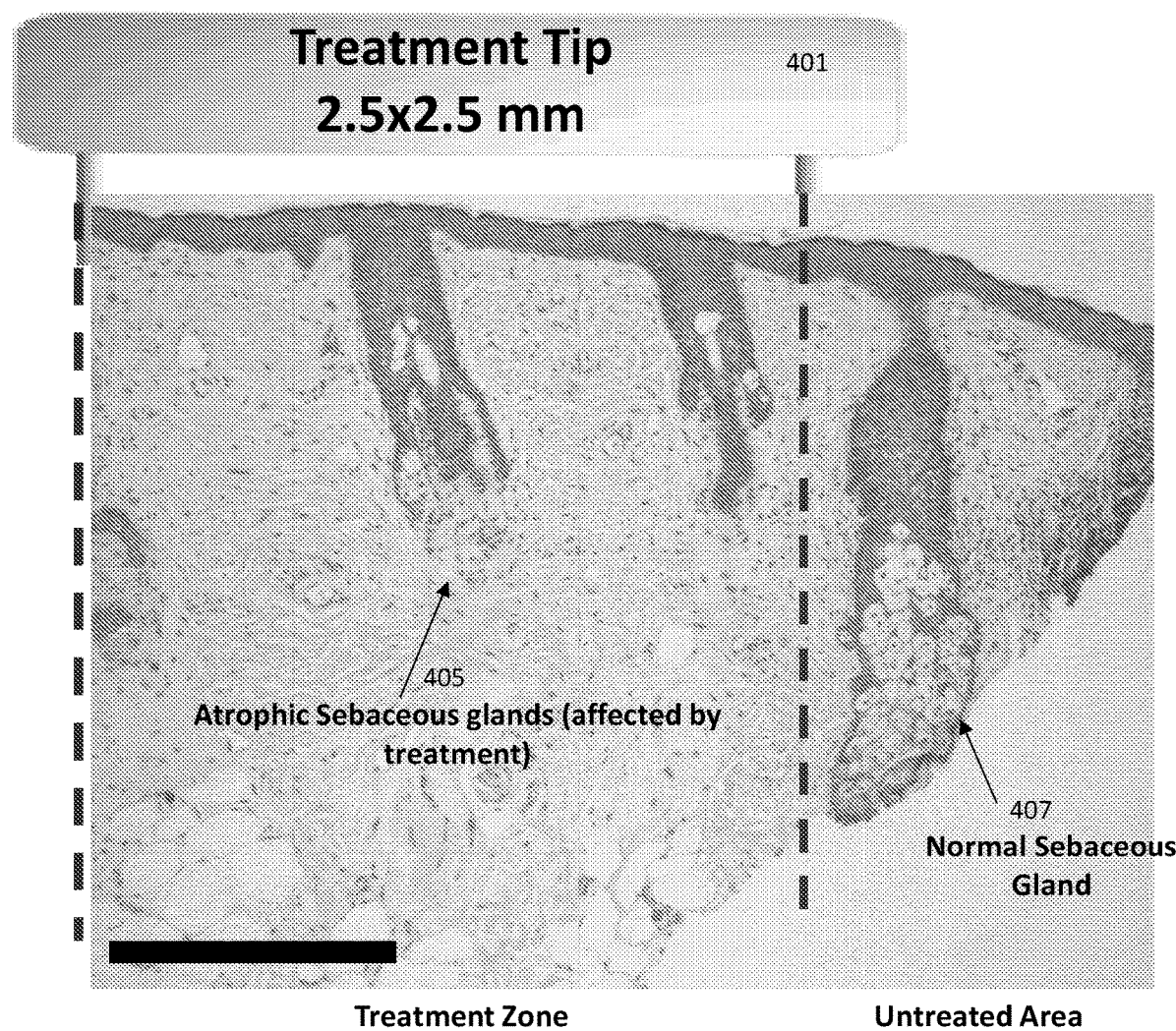
FIG. 4 is an example showing the effect of pulsed electrical energy as described herein to remove or reduce glands within the skin, 30 days after treatment in healthy facial tissue.
Figure 5:
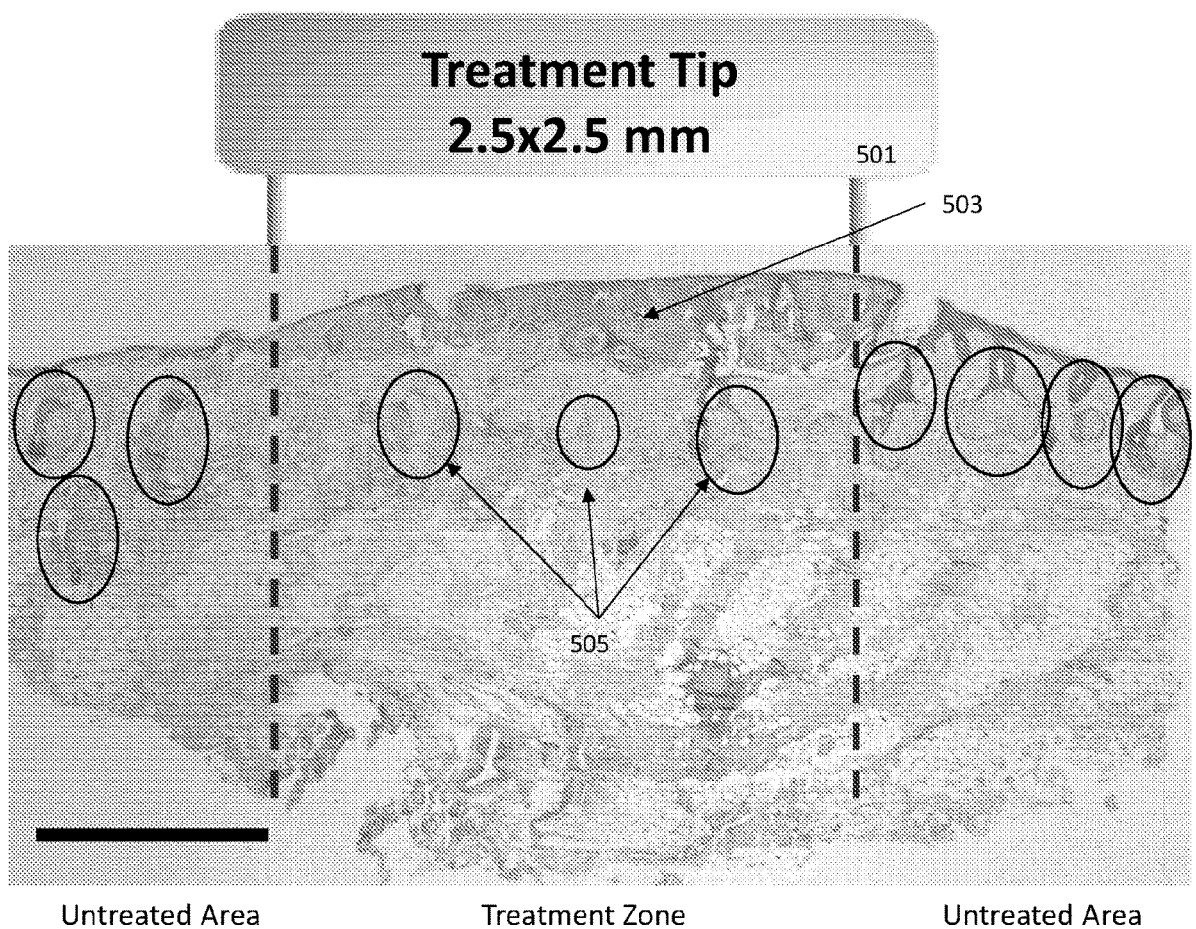
FIG. 5 is another example showing the localized reduction or elimination of glands (e.g., sebaceous glands) in facial tissue 24 hours after treatment with pulsed electrical energy as described herein.

Healthy facial skin was treated in multiple subjects before the tissue was removed, and histological examination of the treated (and nearby control) sites was performed. FIGS. 4 and 5 illustrates the resulting effect on sebaceous glands in treated skin. In FIG. 4, the healthy tissue was initially penetrated by a 2.5 mm×2.5 mm×2 mm (2 mm deep) array of electrodes, a schematically shown by the dashed lines in FIG. 4. The treatment tip 401 schematically shows the treatment tip used. The tissue section shown in FIG. 4 has been stained (e.g., trichrome collagen stains) and the region within the treatment zone (between the dashed lines, representing two of the electrodes from a treatment tip) show a disruption and elimination of the sebaceous glands 405. Only atrophic sebaceous glands remain. The follicles are shown converted to the telogen state following treatment. The region outside of the treatment zone (untreated area) shows normal sebaceous lobules 407. The skin shown was treated by applying nanosecond pulsing (e.g., pulsing between 1 ns and 1000 ns, e.g., 200 ns) at an energy level sufficient to result in destruction of the sebaceous glands within the target skin region. In this example, the epidermis was fully recovered by 30 days post-treatment, with no evidence of dermal damage and no effect on non-cellular dermis.

FIG. 5 shows another example of a section through a facial skin twenty-four hours after treatment to eliminate the sebaceous glands. In FIG. 5 the schematic of the treatment tip 501 is shown, showing a 2.5 mm×2.5 mm (by 2 mm long) applicator tip that was inserted into the skin. In this example, nanosecond pulsing (e.g., an electric field pulsed within the nanosecond range) was applied as described below, at an energy density within the tissue above the minimum threshold sufficient to eliminate the sebaceous gland within the skin. In this example, the pulsed electric treatment affected the sebaceous glands within the treatment zone (e.g., the target skin region between the electrodes, shown by the dashed lines). Twenty-four hours after applying the treatment, a seborrheic keratosis (SK) lesion 503 at the top of the treatment zone is nonviable, and deeper in the target skin tissue region the sebaceous glands (circled) are also undergoing cell death, however acellular dermis is not effected. Structures outside of the treatment zone (e.g., both the left and right untreated areas in FIG. 5) are also unaffected, and have hair follicles with the sebaceous glands that are intact (circled regions in the untreated areas on either side).

FIGS. 6A-6D, 7A-7D, 8A-8D, 9A-9D, 10A-10D and 11A-11D all illustrate examples of time courses of skin treated as described herein to reduce or remove sebaceous glands within the target region of the skin in order to treat sebaceous hyperplasia. SH is a disorder of the sebaceous glands in which they become enlarged, producing flesh-colored or yellowish, shiny, often umbilicated bumps on the face. Each of the target skin regions shown treated in FIGS. 6A-6D, 7A-7D, 8A-8D, 9A-9D, 10A-10D, and 11A-11D include SH lesions and this data was used to examine the efficacy of the treatments described herein. Overall, the pilot study treated SH lesions of the facial skin of 60 different adult subjects; 80% or more of the SH lesions treated were rated clear or mostly clear at 60 days post-treatment.

Figure 3:
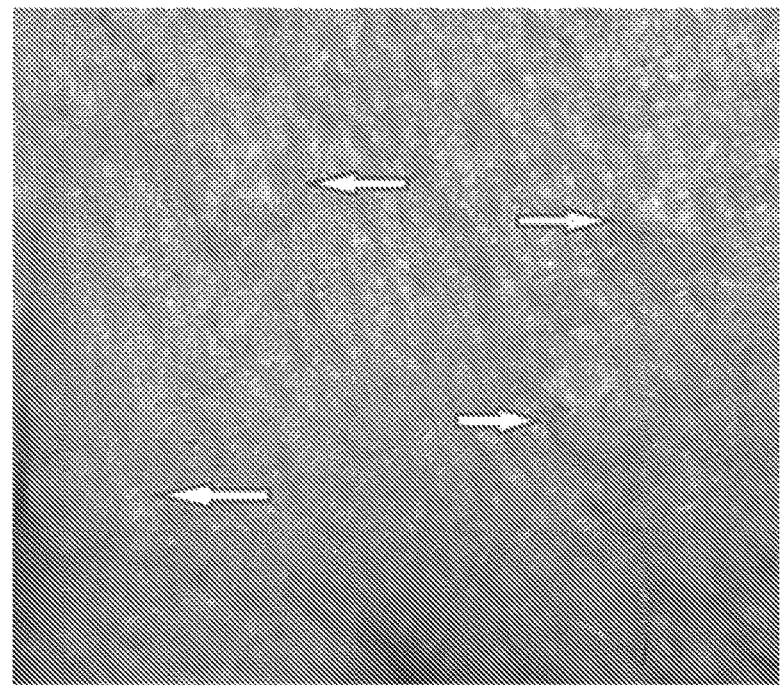
FIG. 3 shows an example of skin with sebaceous hyperplasia (SH) lesions (shown by arrows).
Figures 6A, 6B, 6C, 6D:
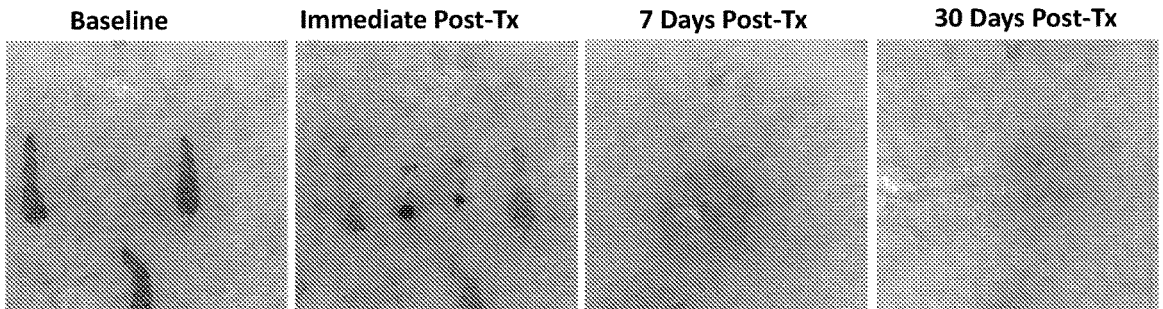
FIGS. 6A-6D illustrate a time course of human skin treated as described herein, showing the elimination, for example, of a SH lesion from a subject's facial area by targeting glands within the tissue while sparing adjacent epidermal and dermal tissue.
Figures 7A, 7B, 7C, 7D:
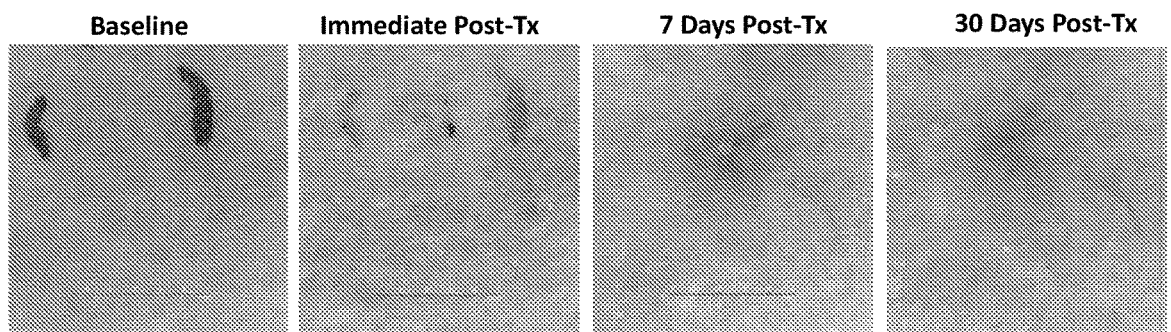
FIGS. 7A-7D illustrate another exemplary time course of a 1.5 mm×1.5 mm region of human skin treated as described herein, showing the elimination of a SH lesion from a subject's facial area by targeting glands within the tissue while sparing adjacent epidermal and dermal tissue.
Figures 8A, 8B, 8C, 8D:
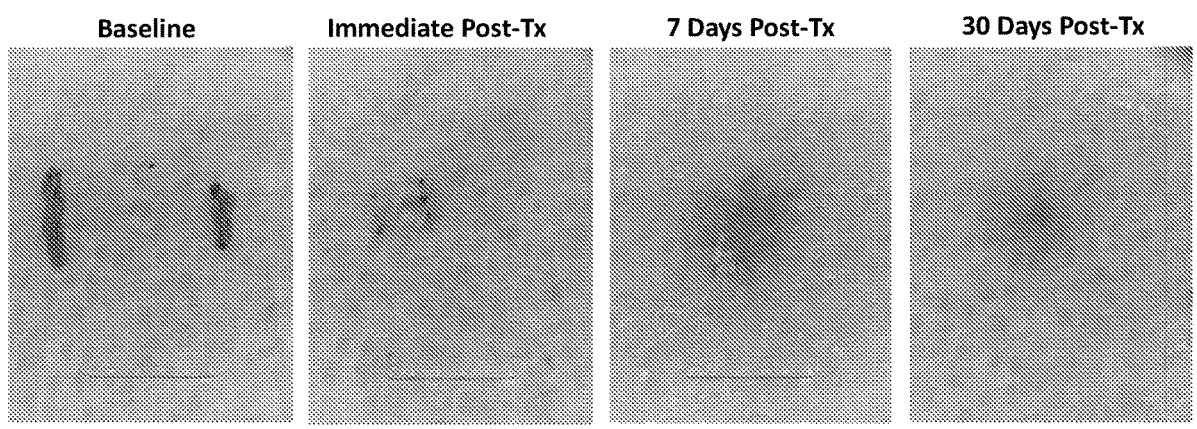
FIGS. 8A-8D illustrate another exemplary time course of a 1.5 mm×1.5 mm region of human skin treated as described herein, showing the elimination of a SH lesion from a subject's facial area by targeting glands within the tissue while sparing adjacent epidermal and dermal tissue.
Figures 9A, 9B, 9C, 9D:
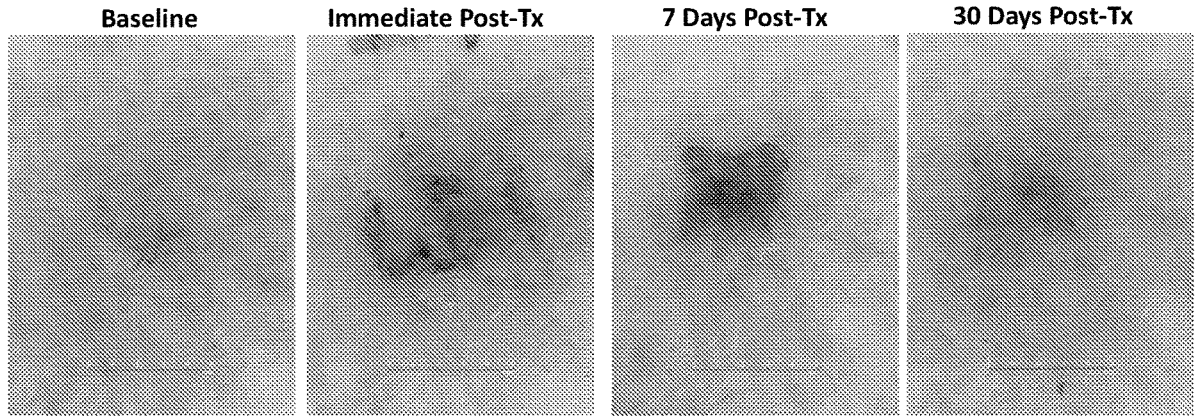
FIGS. 9A-9D illustrate an exemplary time course of a 2.5 mm×2.5 mm region of human skin treated as described herein, showing the elimination, for example, of a SH lesion from a subject's facial area by targeting glands within the tissue while sparing adjacent epidermal and dermal tissue.
Figures 10A, 10B, 10C, 10D:
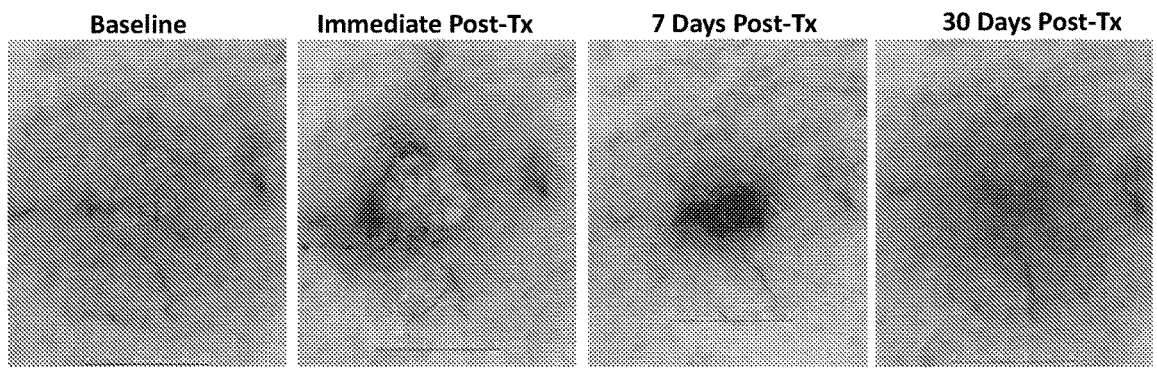
FIGS. 10A-10D illustrate yet another exemplary time course of a 2.5 mm×2.5 mm region of human skin treated as described herein, showing the elimination of a lesion from a subject's facial area by targeting glands within the tissue while sparing adjacent dermal tissue.
Figures 11A, 11B, 11C, 11D:
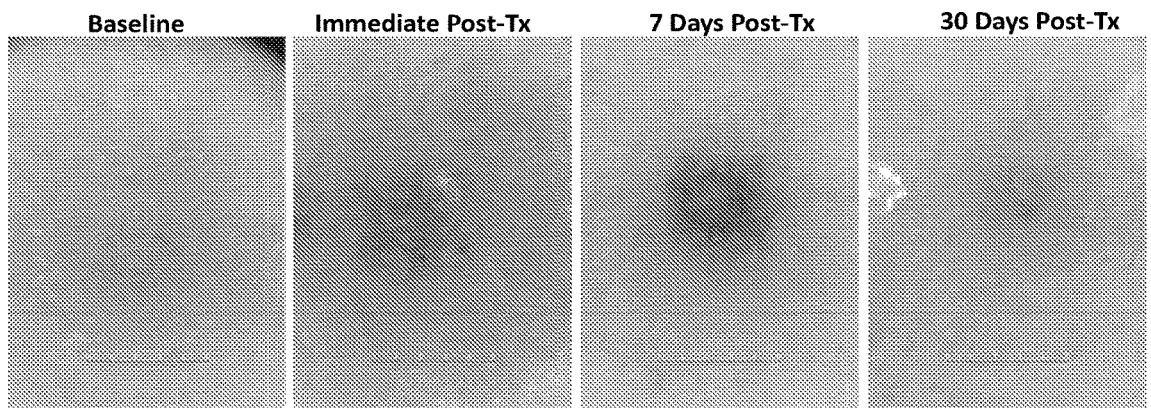
FIGS. 11A-11D illustrate another exemplary time course of a 2.5 mm×2.5 mm region of human skin treated as described herein, showing the elimination of a SH lesion from a subject's facial area by targeting glands within the tissue while sparing adjacent dermal tissue.

For example, FIG. 6A shows an image of the skin including a SH lesion (similar to those shown in FIG. 3, arrows). Fiducial marks are shown on either side of the target skin region. FIG. 6B shows the same region of skin immediately after applying the pulsed electric treatment using a 1.5 mm×1.5 mm treatment tip and delivering pulses having approximately 200 ns to 300 ns pulse width at between 3 kV and 4.5 kV at a frequency range of 4-8 Hz for greater than 150 pulses so that the estimated energy density in the tissue is between 0.01-1.5 J/mm$^3$, including, for example, between 0.06-1.0 J/mm$^3$. FIGS. 6C and 6D show the same region of skin after 7 days and 30 days, respectively, following the treatment. As is apparent from the images, by 30 days the skin appears normal, including the region that formerly included the sebaceous hyperplasia lesion, without any significant discoloration and no scaring.

FIGS. 7A-7D, 8A-8D, 9A-9D, 10A-10D, and 11A-11D all show similar results with different skin regions having SH lesions. FIGS. 7A-7D and 8A-8D were also treated with treatment tips having 1.5 mm×1.5 mm spaced electrodes. FIGS. 9A-9D, 10A-10D, and 11A-11D were treated using larger (2.5 mm×2.5 mm) treatment tips. In all of these examples the SH lesion was completely gone, likely due to the elimination of the underlying sebaceous gland, due to the applied pulsed energy therapy. Complementary histology performed on treated skin regions shows that pulsed electric treatment above a minimum (relatively high) total delivered energy level resulted in reducing or eliminating sebaceous glands, as shown in FIGS. 4 and 5, all without significantly damaging the skin. Since a variety of skin disorders result from dysfunction of the sebaceous glands (e.g., sebaceous hyperplasia, acne, syringoma, rosacea, etc.), these methods may be very useful.

The preliminary results from this work identified treatment levels in which the skin was stimulated sufficiently so that glands (e.g., sebaceous glands) within the treated skin region were eliminated (e.g., de-nucleated) with little or no inflammatory response seen. By 30-60 days, the resulting new skin has little, if any, discoloration and/or scarring and the sebaceous glands had not yet returned.

Figures 19A, 19B:
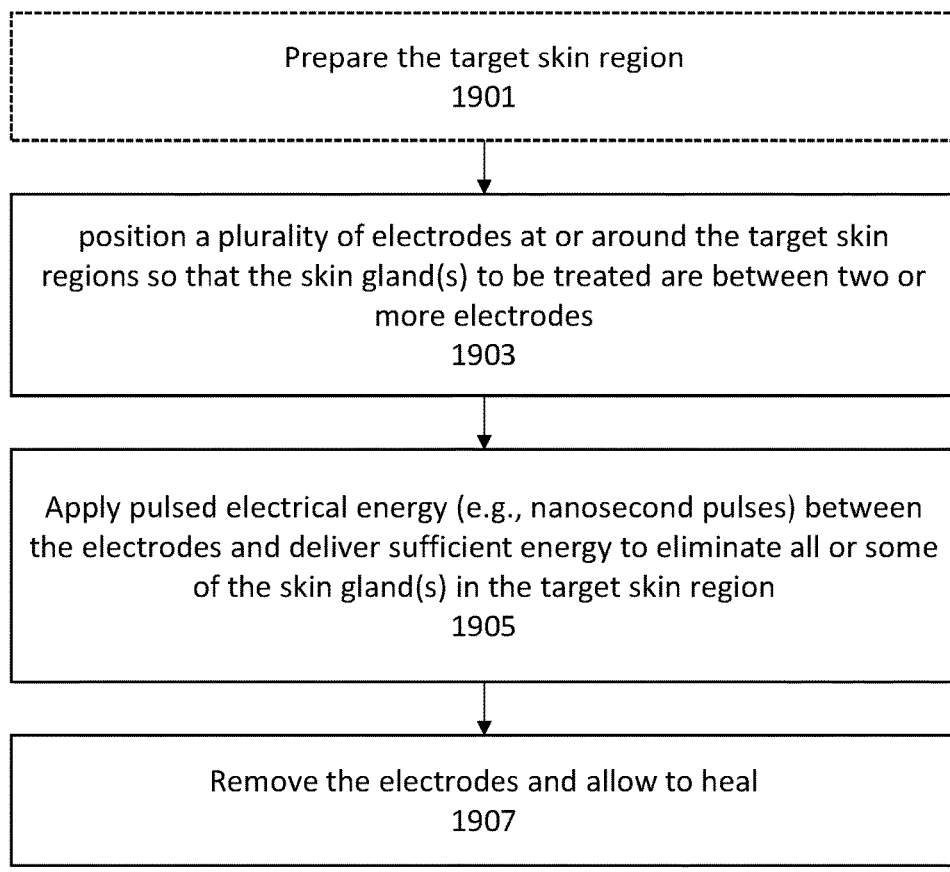
FIG. 19A is a table showing some examples of parameters for applying pulsed energy in the nanosecond range (e.g., between 200 ns-300 ns pulse width) to the skin tissue to eliminate all or some of the glands (e.g., sebaceous glands) within a target region of tissue. This table is based on experimental data such as that illustrated above in FIGS. 4-11D.
FIG. 19B is one example of a method of treating a subject's skin (e.g., to eliminate skin glands and/or to reduce the number of skin glands in a target tissue regions) as described herein.

The methods of using pulsed electric treatment (e.g., pulsed in the nanosecond range) on skin as described herein led to elimination of the glands in the treated region of skin by at least one day post-treatment (likely faster). Interestingly, lower total energy delivered (e.g., less than a threshold energy level) failed to significantly reduce the number of sebaceous glands in the tissue. The table shown in FIG. 19A summarizes some results, showing example treatment parameters for three sizes of tips (e.g., 1.5 mm×1.5 mm, 2.5 mm×2.5 mm, and 5 mm×5 mm). Parameters (e.g., amplitude, pulse width, frequency range and number of applied pulses) for various treatments were varied and effective ranges were examined. Based on the data, effective treatment parameters for reducing or eliminating the sebaceous glands in the target treatment tissue appear to be somewhat dependent on the size of the electrodes, and therefore the energy density within the target tissue (e.g., as seen by the glands in the tissue). For example, energy densities above 0.01 J/mm$^3$ (e.g., greater than 0.02 J/mm$^3$, greater than 0.03 J/mm$^3$, greater than 0.04 J/mm$^3$, greater than 0.05 J/mm$^3$, etc.) are likely to result in reducing or eliminating the sebaceous glands in the target treatment tissue. Additional experiments (data not shown) have validated the data shown in FIG. 19A and have found that the total energy density may be decreased while still eliminating glands in the skin with a high degree of efficacy.

As described in greater detail below, in some variations the amount of energy delivered in a treatment dose may be limited in order to reduce side effects without significantly reducing efficacy. For example, the amount of energy delivered may be limited to less than 3 J, less than 2.5 J, less than 2 J, less than 1.75 J, less than 1.5 J, less than 1.25 J, less than 1 J, less than 0.8 J, etc., for an approximately 2.5 mm×2.5 mm applicator tip. For an applicator tip having an area of between 2 and 3 mm$^2$, the energy density for a treatment may be limited to 0.120 J/mm$^3$ or less (e.g., 0.112 J/mm$^3$ or less, 0.104 J/mm$^3$ or less, 0.096 J/mm$^3$ or less, 0.088 J/mm$^3$ or less, 0.080 J/mm$^3$ or less, 0.072 J/mm$^3$ or less, etc.).

FIG. 19A also illustrates the power applied (e.g., total power applied) by the treatment period, shown as Power (energy per second) in Watts. The power ranges provided in FIG. 19A represent the amount of energy applied to the tissue in one second. The power requirements typically scale with the size of the electrode. For a 1.5 mm×1.5 mm electrode array, the power was between about 0.01 W and about 0.06 W (subsequent data has shown this range may be between 0.01 W and about 0.09 W). For a 2.5 mm×2.5 mm electrode array, the power was between about 0.04 W and about 0.4 W. For a 5 mm×5 mm electrode array, the power was between about 0.2 W and about 3 W (subsequent data has shown this range may be between 0.2 and 0.5 W). Similar results have been observed for 7.5×7.5 mm electrode arrays (e.g., between 0.6 and 1 W) and 10×10 mm electrode arrays (e.g., between 0.8 and 1.2 W). In order to not heat the tissue to the point that thermal damage could occur, the power may be kept below a predetermined level. Thermal damage may depend on many variables, including how long the tissue is heated. For the given parameters shown in FIG. 19A, no thermal damage was seen. In some variations, for powers at the higher end of the range, e.g., 1 to 3 Watts, the treatments were applied fast in order to avoid thermal damage to the tissue.

FIG. 19B schematically illustrates one method of treating a region of skin to reduce or eliminate glands within the target region of skin. This method may be for cosmetic treatments. In the optional step (1901) the target region of skin may initially be prepared, which may include washing, drying and/or treating with a medicament, such as a pharmaceutical composition (e.g., an antibiotic, anesthetic, etc.). Furthermore, in some implementations, as a preliminary step, a device for applying electrical pulses may be precisely positioned relative to the treatment area as further described in detail in reference to FIGS. 20-26B. Thereafter, the treatment method begins by applying pulsed electrical energy (e.g., within the nanosecond range of 0.1 ns to 1000 ns) to the treatment zone (e.g., target region of the skin including one or more target glands), for example, by inserting a plurality of tissue-penetrating electrodes into the subject's skin (1903). When treating the skin to reduce or remove undesired lesions, for example, sebaceous hyperplasia lesions, skin-penetrating electrodes may be inserted around and/or into the sebaceous hyperplasia lesion on the skin, for example. In general, however, the boundary of the target region may be set by the border defined by the electrodes. When tissue penetrating (e.g., needle) electrodes are used, the electrodes may be inserted to any appropriate depth, for example, any depth between 1 mm and 5.5 mm, typically about 2 mm into the skin. The depth of insertion may depend on the depth of the target glands, which are typically between 1-3 mm deep for sebaceous glands, for example. Other glands may be even deeper, for example, 5 mm deep. The target electrode may be inserted to the depth of the gland, or slightly above and/or below the targeted gland.

In general, methods described herein, including the method illustrated in FIG. 19B, may be for treatments of cosmetic indications. Such cosmetic indications typically have no symptoms other than the visible effects being treated and, while annoying and may lead to negative psychosocial consequences, are generally without medical consequences. For example, a sebaceous hyperplasia (SH) is one example of a cosmetic indication. SH treatment is considered an aesthetic/cosmetic treatment as SH is generally painless and generally without medical implications. Other cosmetic indications for which the methods and apparatuses described herein may be effectively used to treat may include: acne (particularly mild, temporary acne), oily skin, rosacea/rosacea-like dermatitis (a redness of the skin, typically on the cheeks), steatocystoma (e.g., benign cysts in the sebaceous gland), hyperhidrosis (e.g., excessive sweating), bromhidrosis/osmidrosis (e.g., body odor caused by overactive apocrine glands), chromhidrosis (sweating that produces a colored substance that stains clothing), hidradenitis suppurativa (benign sweat gland tumor), rhinophyma (swelling and inflammation of the nose at least partly caused by overactive sebaceous glands) and syringoma (small raised whitish lesion, typically on lower eyelid). Other cosmetic indication may include: xerosis cutis, asteatosis, seborrhea/seborrheic dermatitis.

Figure 27A:
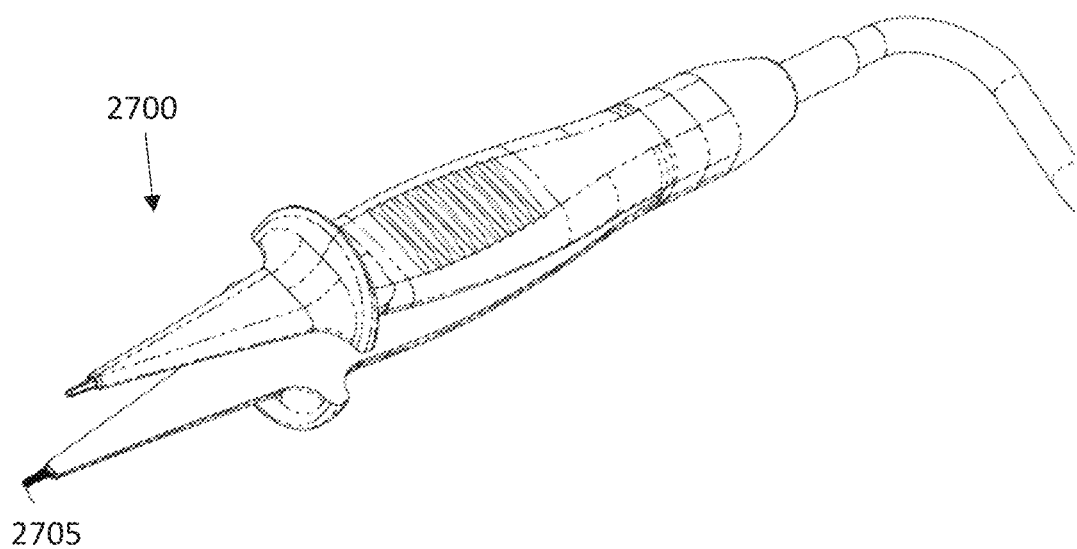
FIG. 27A illustrates one example of an applicator configured as a pair of electrodes arranged in a forceps configuration, with one or more electrodes one each of two arms arranged so that tissue (e.g., a target region of skin) may be held between the arms to deliver a pulsed electrical energy as described herein.
Figure 27B:
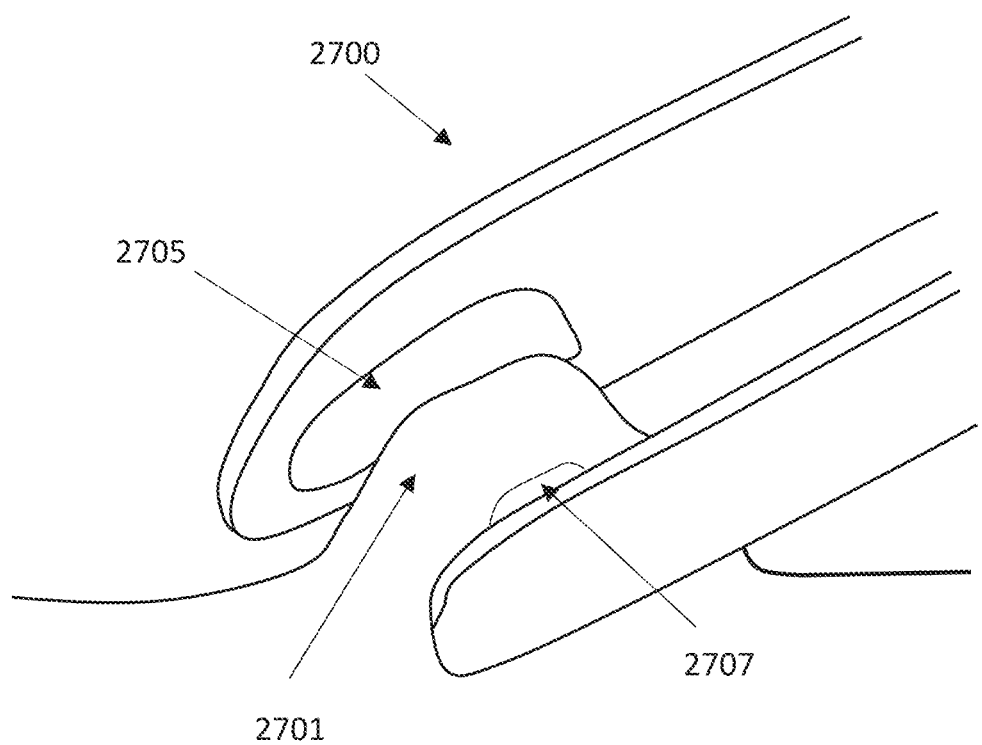
FIG. 27B illustrates one example of an applicator configured as a forceps including a plurality of electrodes that may be used to apply energy to a region of tissue.

In some variations, non-penetrating electrodes may be used. For example, the tip shown in FIG. 12D illustrates one example of a treatment tip having non-penetrating electrodes. In some variations, the target skin region may be held or positioned so that they are between the electrodes without penetrating the skin (or in addition to penetrating the skin). For example, the electrodes may be part of a pair of grasping jaws (e.g., a forceps-like structure, which may be formed as a forceps-like electrode), as illustrated in FIGS. 27A and 27B. As shown in FIG. 27A, the applicator, which may be configured as an applicator tip, is configured as a forceps 2700 and includes a pair of arms that each include one or more electrodes 2705 on the distal tip region. As shown in FIG. 27B, tissue 2701 (e.g., skin tissue) including a target such as a SH lesion or other gland 2707 may be pinched and held between the two or more surface electrodes 2705 of the forceps-like electrodes. The jaws of the applicator may be opened and the target tissue (e.g., a region including a lesion such as an SH lesion) may be held between the jaws and therefore the electrodes, pushing the electrodes into the skin (but not penetrating the skin). Thus, the lesion may project up in between the jaws (or alternatively, the jaws may push down the skin on either side of the jaws surround the target tissue region, on each side).

In step (1905), pulse electrical energy (for example, energy having a pulse width within the nanosecond range, such as between 0.1 ns and 1000 ns) may be applied so that the amount of energy delivered during the treatment (e.g., the treatment dose) seen by the target gland is equal to or above the minimum threshold for eliminating the gland (e.g., in some examples, energy densities above 0.001 J/mm$^3$ (e.g., above 0.005 J/mm$^3$, above 0.01 J/mm$^3$, above 0.02 J/mm$^3$, 0.03 J/mm$^3$, etc.). In any of these methods, the energy density applied may be limited to reduce the likelihood of negative side effects such as hyperpigmentation and/or volume loss, as will be described in greater detail blow.

Following the treatment, the electrode(s) may be removed from the tissue and the tissue allowed to recover 1907. During the first 24 hours following treatment, the cells forming the gland will be eliminated. It is hypothesized that during or immediately after the treatment the cell is de-nucleated by the applied energy, resulting in the destruction and absorption of the cell by the body. After the skin has recovered (e.g., typically within 30-60 days following the treatment), the abnormal (e.g. causing hyperplasia) glands are gone; and new normal glands may form. In the context of the treatment of sebaceous hyperplasia, the newly-formed sebaceous glands may be non-hyperplastic compared to the eliminated glands.

It will be apparent that the number of steps of the methods that are utilized are not limited to those described above. Also, the methods do not require that all the described steps are present. Although the methodology described above as discrete steps, one or more steps may be added, combined or even deleted, without departing from the intended functionality of the embodiments of the disclosure. The steps can be performed in a different order or have the steps shared between more than one processor, for example. It will also be apparent that the method described above may be performed in a partially or substantially automated fashion, including performed using robotic systems.

For example, to assist with precise placement of the plurality of electrodes relative to the treatment area (e.g., the lesion to be treated), any of the methods and apparatuses (e.g., systems) described herein may include a targeting patch (also referred to herein as a guide patch) that may be used to assist in positioning of the treatment tip(s).

A targeting patch may be insulated, and/or may include an insulating barrier that may be penetrated by the plurality of (e.g., tissue-penetrating) electrodes. The targeting patch may also include one or more alignment structures that may extend from (and/or project into) the targeting patch to engage with the tip of the applicator or may otherwise act as a guide to hole or steer the applicator tip to the target tissue region. In some variations the central region (the region to be penetrated by the electrode(s), may be transparent and/or translucent, to allow the user to align the targeting patch over the region to be treated. The targeting patch may be used in conjunction with a marker or stain that may be visualized or visualizable through the target region (e.g., a central region or other portion through which the electrodes will penetrate). For example, the skin may be marked at the lesion with a marker that may be visualized through the target treatment zone of the patch. These targeting patches may therefore prevent or reduce arcing and may increase the accurate targeting of lesions. These targeting patches may be used with or, preferably, without an additional dielectric substance on the treatment tip prior to inserting the needles into the tissue. Without the targeting patch, a dielectric material (e.g., gel, such as petroleum jelly) may be placed on the tissue over the lesion and may surround the electrode(s) (e.g., needles), filling any air gaps caused by tenting of the tissue relative to the electrodes, and may seals the tip of the applicator to the tissue, which may greatly reduce the instance of surface arcs. A transparent or semi-transparent targeting patch as described herein may be placed over the lesion prior to treatment, and may ensure a sufficient amount of dielectric is in place for the treatment and removes the need to clean the tip between treatments. The targeting patch may also enhance targeting of the tissue (e.g., a lesion on the tissue). Alternatively, a user may place a template over the lesion and, using a surgical marker, places fiducial (e.g., hash) marks on the skin to guide the instrument placement. These fiducial marks may then be aligned with fiducials on the treatment tip (see, e.g., FIGS. 16A-16B, above). As mentioned, alternatively, a treatment targeting patch may be used which may include integrated fiducial markings and/or an engagement region that engages with the tip to ensure proper alignment.

Figure 20:
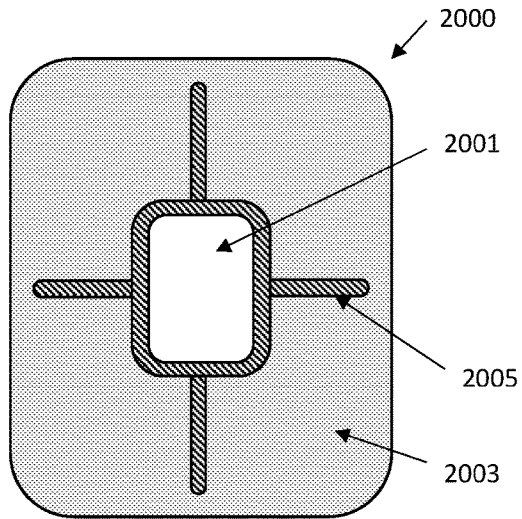
FIG. 20 is one example of a targeting patch (e.g., also referred to as a targeting pad) that may be used in any of the methods or included as any of the apparatuses (e.g., systems) described herein.

For example, FIGS. 20-26B illustrate examples of targeting patches (e.g., targeting patch devices) that may be used to guide and/or to insulate a treatment tip and may be placed on the tissue to be treated prior to treatment. FIG. 20 is an example of one variation of a targeting patch 2000. The targeting patch 2000 may be made of any appropriate material, particularly electrically insulative materials, including, e.g., a silicone. The targeting patch may have an adhesive on at least one surface so that it may be held in position around the target tissue region. In addition, the targeting patch may include a target region (e.g., shown as a central region 2001) that is a representation of the treatment zone so the user can correctly place the patch over the skin region to be treated. The target region may also be referred to as a treatment tip engaging region. In some variations the target region is an opening, or a plurality of openings through which electrodes from the treatment tip may enter the underlying tissue. In some variations a dielectric material may be paced into the opening once it is positioned on the tissue. Alternatively, the target region may include a dielectric material having a predetermined thickness; the covering dielectric material in the target region may be formed of the same, or a different, material than the rest of the targeting patch. For example, the treatment zone region 2001 may include a thickness (e.g., between 0.1 mm and 5 mm, less than 2 mm, less than 1 mm, etc.) of a dielectric material through which the needle electrodes may penetrate in order to contact (and penetrate into) the tissue. The dielectric material may help prevent arcing between electrodes, and on some types of electrodes, may replace the need for coupling gel between the electrode and the skin. The targeting patch may also include one or more fiducial marks 2005 that may be used to align with (and in some variations, engage with) the treatment tip. The fiducial marks may be a different color, raised, sunken, or a combination of the above, to engage with the tip of the applicator.

Figure 21:
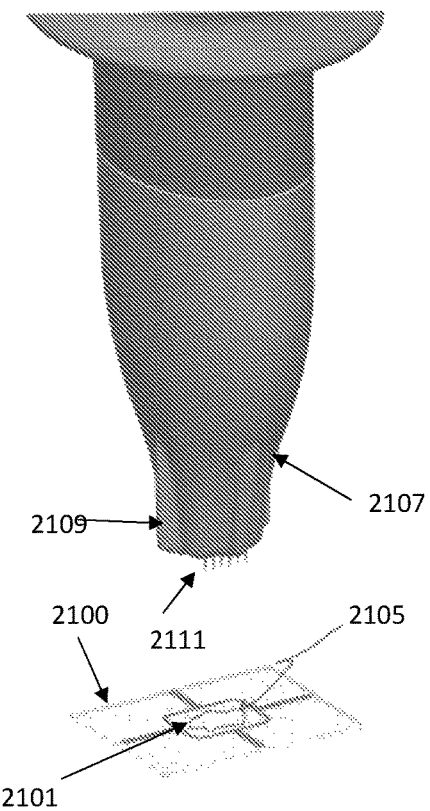
FIG. 21 illustrates the use of a targeting patch, such as the one shown in FIG. 20, to guide the application of an electrode applicator tip onto the target tissue region.

FIG. 21 shows an example of a targeting patch 2100 placed over a lesion 2105 with the lesion in the treatment zone 2101. FIG. 21 shows the treatment tip ready for treatment, fiducials 2109 on the tip 2107 aligned with fiducial marks on patch so that the needle electrodes 2111 may penetrate through the insulating thickness of the treatment zone and bracket the target tissue (including the lesion 2105).

Figure 22A:
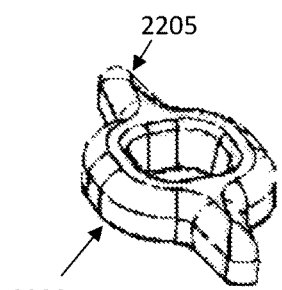
FIGS. 22A-22C illustrate variations of targeting patches that may be used.
Figure 22B:
Figure 22C:
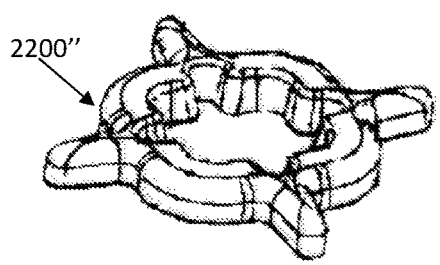
Figures 23A, 23B:
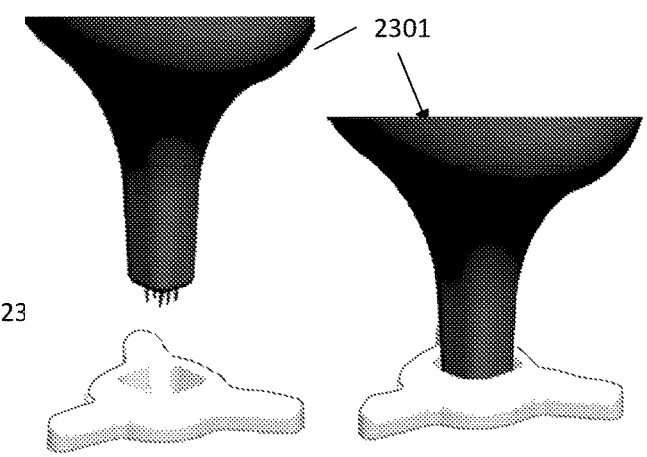
FIGS. 23A-23B illustrate the operation of one variation of a targeting patch as described herein.
Figure 24A:
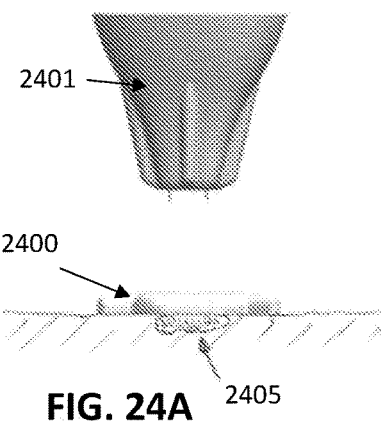
FIGS. 24A-24B show another illustration, from a side view, of a targeting patch similar to that shown in FIGS. 23A-23B.
Figure 24B:
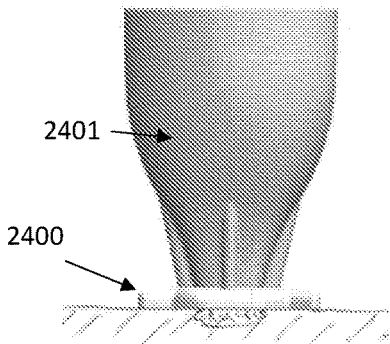

FIGS. 22A-22C illustrate variations of targeting guides 2200, 2200', 2200" as described herein. The targeting guides may have a thickness of between 0.1 mm and 10 mm or more. The guides may be thick enough to physically engage with and mechanically align the electrode to the target lesion. FIGS. 23A-23B illustrate the use of a targeting guide placed onto a tissue so that the treatment tip 2301 may dock with the targeting guide 2300. This docking action may mechanically align the electrode(s) with the target tissue (including any target lesion); the user may perform this docking without the need to visually align the fiducials. Similarly, FIGS. 24A and 24B show a side perspective view of a targeting guide 2400 positioned over a lesion 2405 and used to guide and insulate a treatment tip 2401 including needle electrodes. Thus, in any of these targeting patch devices, the target region or a lip at least partially surrounding the opening formed by the target region, may engage with the treatment tip in a keying manner. For example, the target region may be keyed to the shape of the treatment tip.

Figure 25A:
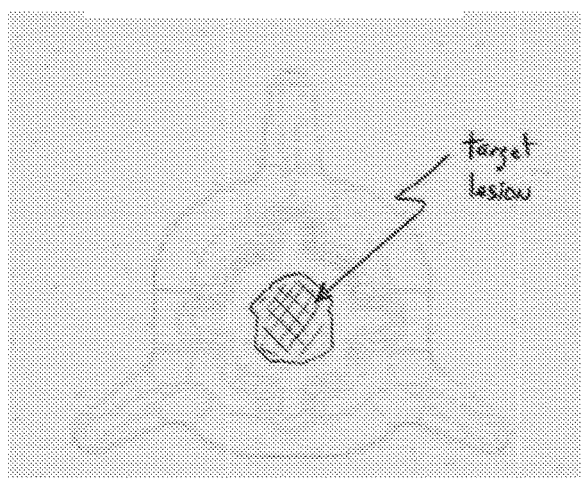
FIGS. 25A-25B show top and bottom perspective views, respectively, of another variation of a targeting patch.
Figure 25B:
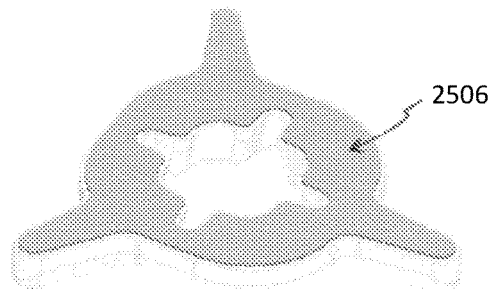
Figure 26A:
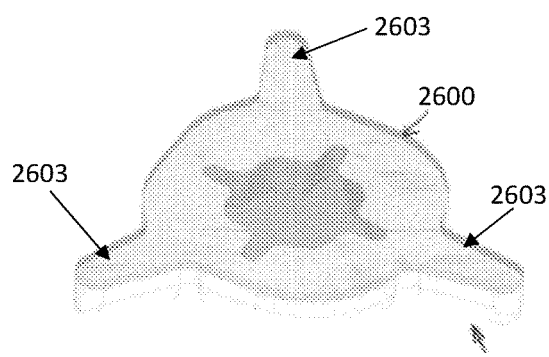
FIGS. 26A-26B show top perspective and bottom perspective views, respectively, of an example of a targeting patch as described herein.
Figure 26B:
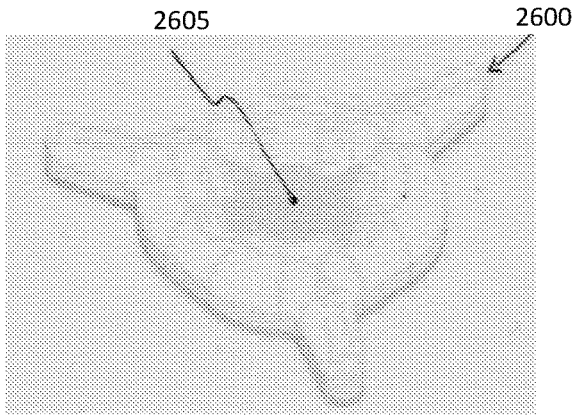

FIGS. 25A-25 illustrate another example of a targeting guide, showing a top (FIG. 25A) and bottom (FIG. 25B) view. The bottom view shown in FIG. 25B also includes an adhesive material 2506 that may secure the targeting guide to the tissue (e.g., skin). The adhesive material may be a biocompatible adhesive. FIGS. 26A-26B illustrate another example of a targeting guide 2600 formed of a transparent dielectric material, such as silicone. The bottom layer show in FIG. 26B includes a region of the same transparent dielectric material covering the target region 2605. The dielectric material in this region could be thinner, thicker, or the same thickness as other regions of the targeting guide. Grasping extensions 2603 (e.g., bosses) may allow the user to easily grasp the targeting guide and properly position the targeting guide over the target lesion.

According to another aspect of the present disclosure, an apparatus for treating skin tissue to reduce or eliminate skin glands, and therefore to prevent or treat a disorder of a skin gland (e.g., acne, sebaceous hyperplasia, etc.) is provided. The apparatus may include a pulse generator; a set of electrodes; and a controller configured to control, at least partially, operation of the pulse generator. The controller may comprise a processor having a set of instructions, wherein the set of instructions, when executed by the processor causes the pulse generator to generate and apply through the set of electrodes a pulsed electrical treatment to a region of tissue to eliminate skin glands within the target tissue region (e.g., by de-nucleated cells of the glands) without provoking a substantial inflammatory response. Any of the apparatuses described herein may include, for example, a hand-held applicator having a hand piece. For example, FIG. 12A shows an example of a hand piece 1201 that may plug (via cord 1203) to a generator (not shown) for generating the pulsed electrical energy. One or more different tips may couple with the hand piece; the tips may include the electrode(s) for delivering the energy to the skin, as described above. For example, FIGS. 12B-12D, and 14-16, illustrate exemplary electrode tips for treating skin by delivering pulsed electrical energy as described herein. In FIG. 12A, the tip 1205 fits over the distal end of the hand piece 1201, and snaps or locks in place once electrical contact is made with the projecting (needle-like) electrodes 1211. For example, the tip may be mechanically secured (e.g., by snap-fit, friction fit, etc.) onto the end of the hand piece. In FIG. 12B, two electrodes are provided, and each is sufficiently sharp so that it may penetrate the skin. One electrode may be the cathode and the other electrode the anode. The electrodes may be pointed and/or sharp, or otherwise configured to penetrate the tissue. The region between the electrodes may be adapted to fit over a skin lesion that projects from the skin. FIG. 12C shows a tip 1207 that includes two parallel rows of sharp, tissue penetrating electrodes that may all simultaneously penetrate the skin in the region including or surrounding the target skin region. Alternatively, only some of the electrodes may penetrate the skin. In this example, the electrodes (or electrode pairs) may be separately addressed by the apparatus, or they may be connected together. For example, in FIG. 12C, the left row of electrodes may be electrically connected (e.g., acting as a cathode) and the right row of electrodes may be electrically connected (e.g., acting as an anode).

FIG. 12D illustrates an example of a non-penetrative (e.g., surface) tip 1209 including electrodes that are configured to deliver, for example, pulsed electrical energy as described herein. In FIG. 12D, an outer ring of electrode surrounds an inner electrode; these electrodes may act as an electrode pair for delivering energy (e.g., current) to the skin. The tips in FIGS. 12B-12D may be swapped. While not shown, instead of being hand-held, an applicator may be configured for attachment to a movable arm of the robotic system. The movement and/or operation of such applicator may be computer-controlled.

FIG. 13 illustrates an example of an applicator tip including needle electrodes that are configured to deliver electrical energy, as described herein. In this example, a plurality of outer electrodes (e.g., ground electrodes) surround an inner electrode (e.g., delivery electrode).

Figure 14A:
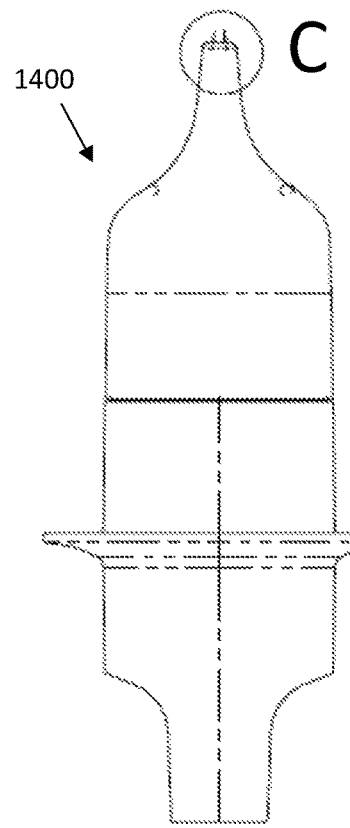
FIGS. 14A-14F illustrate an example of an applicator tip with a plurality of needle electrodes, showing an array of six electrodes forming a 1.5 mm×1.5 mm box.
Figure 14B:
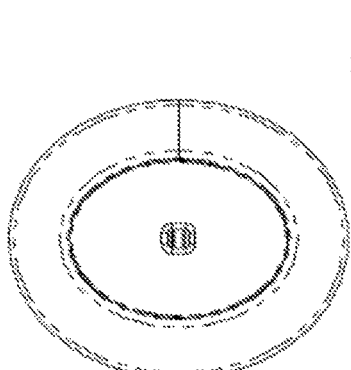
Figure 14C:
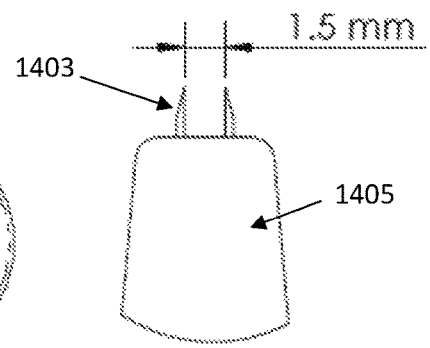
Figure 14D:
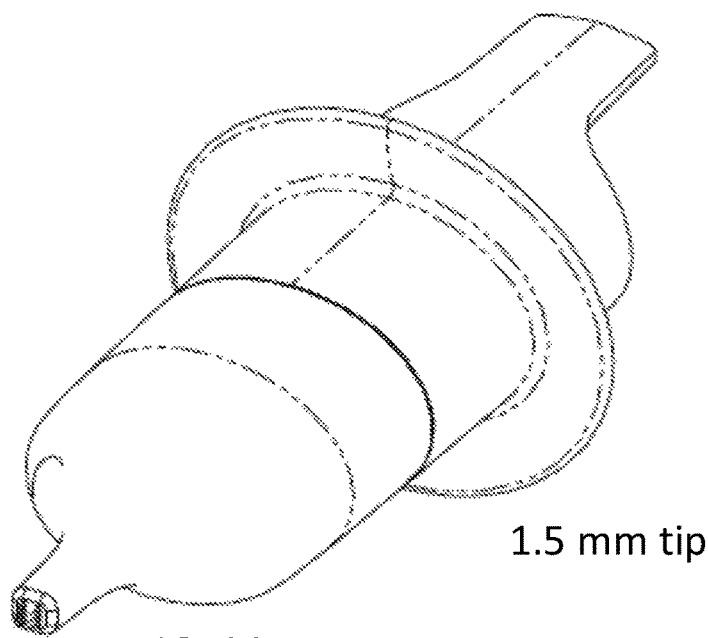
Figure 14E:
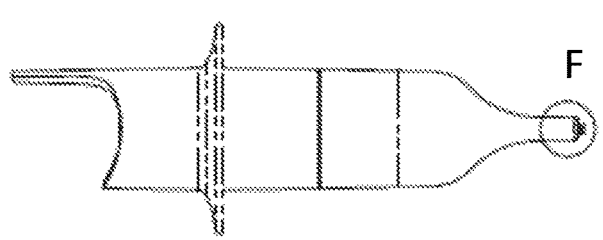
Figure 14F:
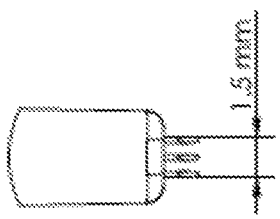
Figure 15A:
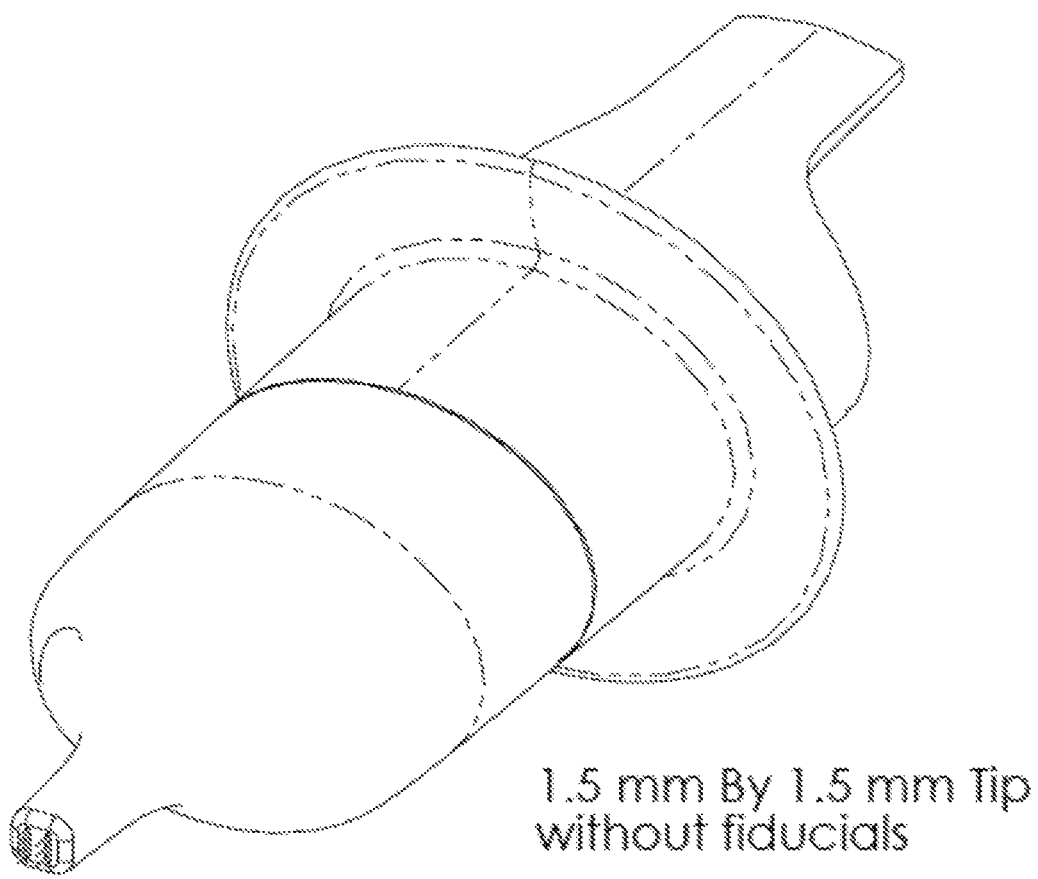
FIGS. 15A-15B illustrate another example of an applicator tip with an array of electrodes (e.g., needle electrodes). The two lines of electrodes (extending 1.5 mm) are spaced 1.5 mm apart.
Figure 15B:
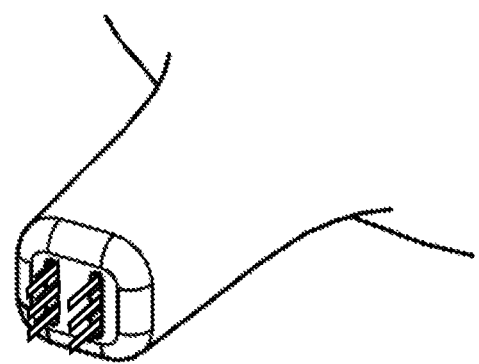

FIGS. 14A-14F show different views of one example of a treatment tip similar to that used to treat the target tissue regions shown in FIGS. 6A-6D, 7A-7D, and 8A-8D, above. In this example the treatment tip is shown that may be attached to the hand piece or other component for connection to the controller and generator. FIGS. 14C and 14F show enlarged views of the distal end of the tip 1400, including the six electrodes 1403 extending from an insulated base 1405. Similarly, FIGS. 15A-15B show perspective views of a 1.5 mm×1.5 mm, including an enlarged view of the electrode extending (2 mm) from the base of the electrode tip region. While some applicator tips may comprise fiducials, the example of the applicator tip of FIG. 15A does not have fiducials.

Figure 16A:
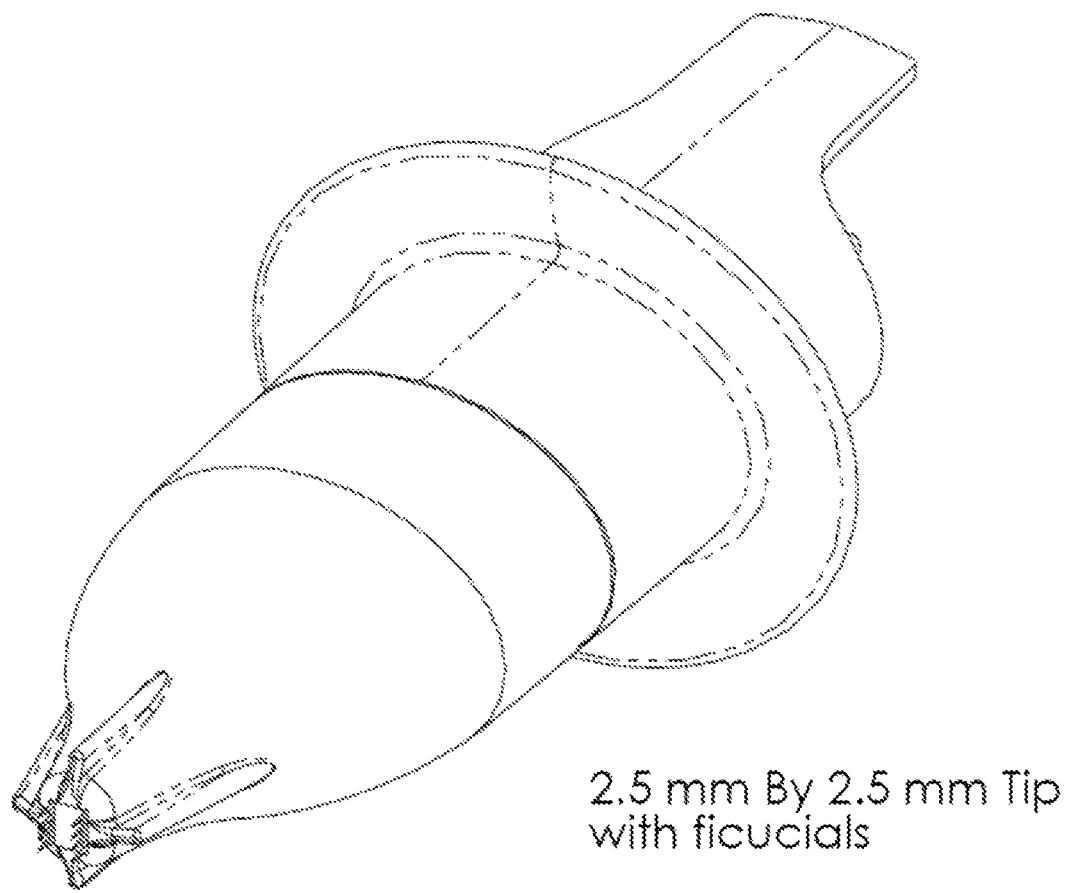
FIGS. 16A-16B illustrate another example of an applicator tip with an array of electrodes (e.g., needle electrodes). The two lines of electrodes (extending 2.5 mm) are spaced 2.5 mm apart.
Figure 16B:
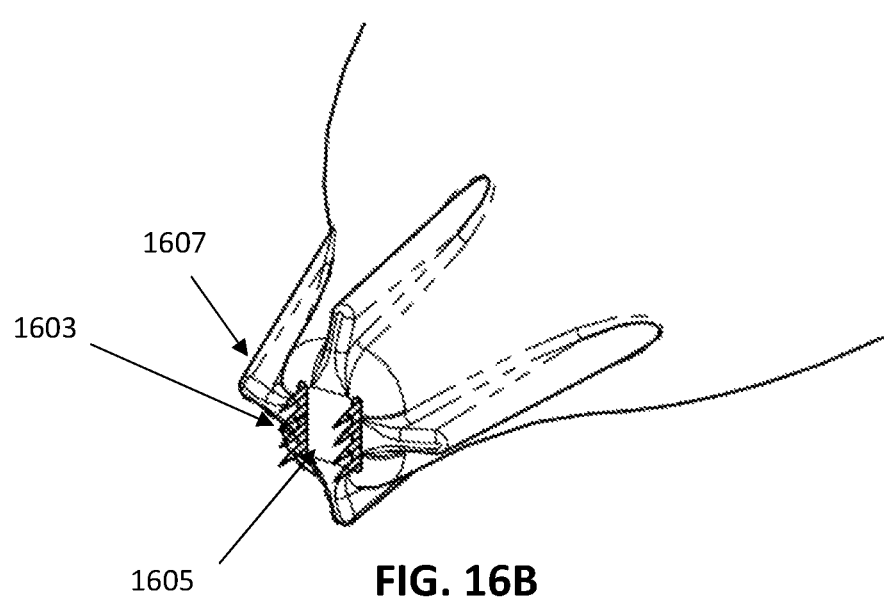

FIGS. 16A and 16B shows an alternative view of a tip of an applicator that includes eight electrodes 1603 extending from the base 1605. In this example the applicator tip also includes fiducial marking regions 1607 that form a "+" shape with the electrodes in the central region. The fiducial alignment region may be used to align the treatment tip with the target region of the skin.

Figure 17A:
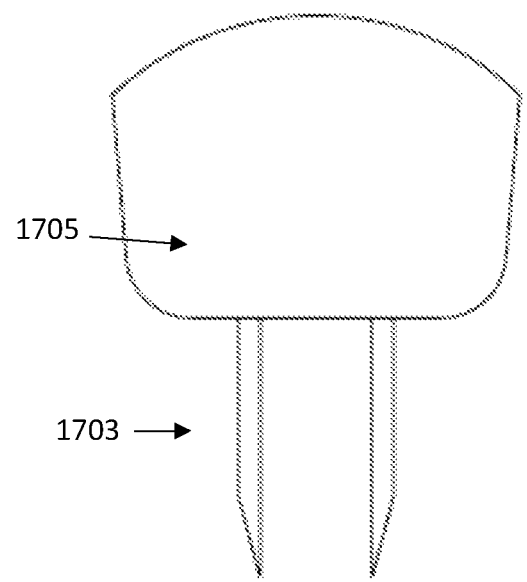
FIGS. 17A-17D illustrate examples of electrodes (shown as needle electrodes).
Figure 17B:
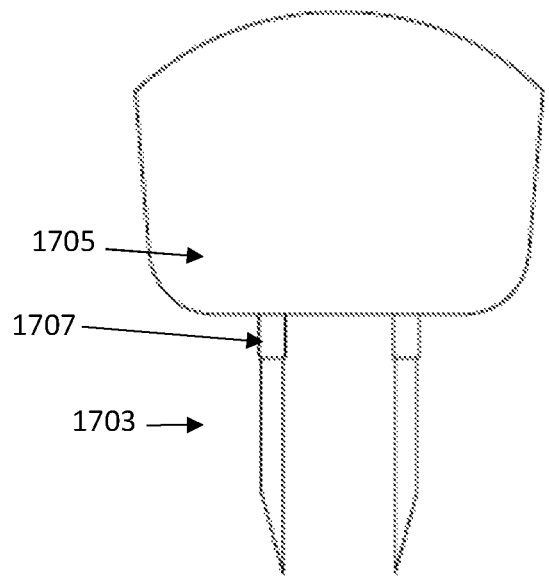
Figure 17C:
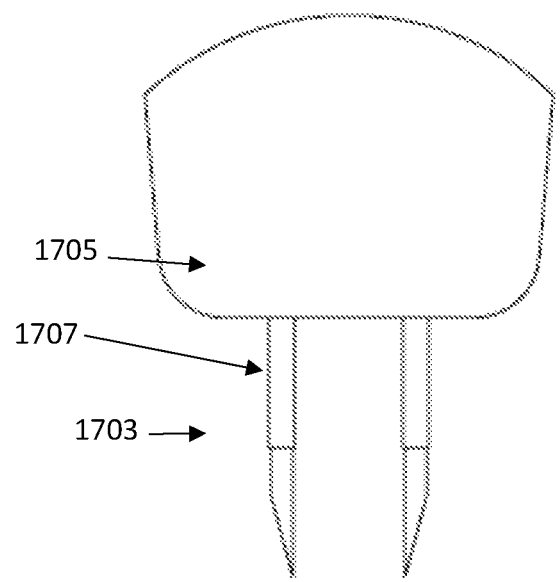
Figure 17D:
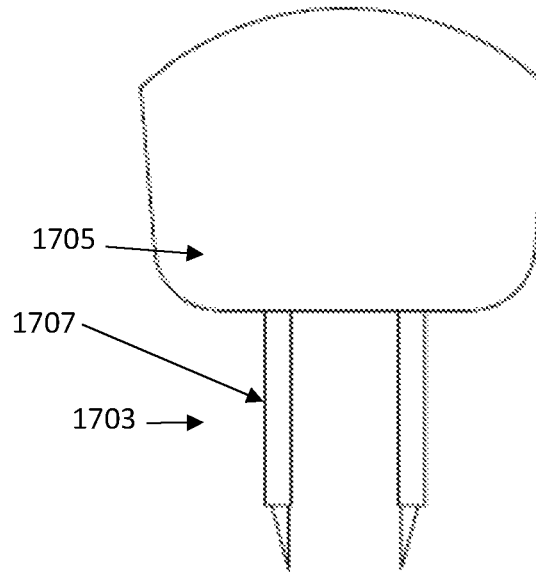

In any of the variations described herein, the treatment tip may include insulated (or partially insulated electrodes). Specifically, the tissue-penetrating electrodes may be insulated over the region near the base of the electrode to limit the energy applied at this region, which will correspond to the more surface region of the tissue when the electrode have been inserted into the skin. Typically, the target glands (e.g., sebaceous glands, eccrine glands, or apocrine glands) may be located between 1-5 mm deep into the skin; thus it may be desirable to target this depth of the tissue specifically; this targeting may be achieved by electrically insulating the portion of the tissue-penetrating electrodes that extend above and/or below the depth of the target gland (e.g., the cell body of the gland). For example, FIG. 17A shows an example of a pair of electrodes 1703 extending from a base 1705. The base may be electrically insulated. The electrodes may extend, for example, 1-2 mm or more. Any portion of these electrodes may be insulated, as shown in FIGS. 17B-17D. The extent of the insulation 1707 on the electrodes may be selected to protect the dermis and/or epidermis, and particularly to protect the adnexal structures near the skin and other structures adjacent to the target gland. Since the target glands may be at about 1 mm and deeper, the region between the base 1705 and about 1 mm may be insulated, as shown in FIG. 17B and 17C. Alternatively, the majority of the electrodes 1703 may be insulated 1707, as shown in FIG. 17D.

In some variations, the electrodes applying the energy may be rotated partway through the application of the treatment. In some implementations, automated, including computer controlled, systems may provide precise and accurate rotating and repositioning of the energy delivery device (e.g., rotation of the electrode pattern) in the same treatment region or zone. Rotation, as used here, may refer to the rotation of the pattern of two or more electrodes, including (but not limited to) tissue penetrating electrodes, such as needle electrodes. Rotation of the pattern of electrodes may be relative to a target tissue region. In general, the rotated pattern may be rotated by any amount of rotation (e.g., between 0.5 degrees to 359.5 degrees, such as between 5 degrees and 355 degrees, between 10 degrees and 350 degrees, between 20 degrees and 340 degrees, between 30 degrees and 330 degrees, between 40 degrees and 320 degrees, approximately 90 degrees, etc.). The rotation may be clockwise and/or counterclockwise. Rotation may be physical rotation of the pattern of electrodes (e.g., the applicator) relative to the tissue, or rotation by changing the active electrodes of an array of electrodes so that the pattern of active electrodes is rotated relative to the target tissue. The pattern of electrodes may be rotated relative to a region of tissue (e.g., a target region of tissue) so that after rotation the treatment is applied to the same region of tissue. For example, the treatment tip may be positioned on the same region of the tissue before and after rotation. Any of the apparatuses described herein may be implemented in robotic systems that may be used to position and/or control the electrodes during a treatment. For example, a system may include a robotic arm to which is coupled an applicator, such as an energy delivery device, having an applicator tip with a plurality of electrodes. Various motors and other movement devices may be incorporated to enable fine movements of an operating tip of the applicator in multiple directions. The robotic system may further include at least one image acquisition device (and preferably two for stereo vision, or more) which may be mounted in a fixed position or coupled (directly or indirectly) to a robotic arm or other controllable motion device. The operating tip of the applicator may be positioned over a tissue region to be treated.

In some variations, the applicator tips may be configured so that the electrodes (e.g., needle electrodes) are protected when not in use, for example, covered with a retractable insulating cover. The cover may include holes or opening through which the electrodes may extend when the electrode housing is pushed proximally. In some variations the insulating cover does not include holes or openings and instead the treatment electrodes penetrate into and through the soft insulating cover itself. In further embodiments, the electrodes themselves may be movable to extend and retract from the electrode housing (with or without any insulating cover).

Figure 18A:
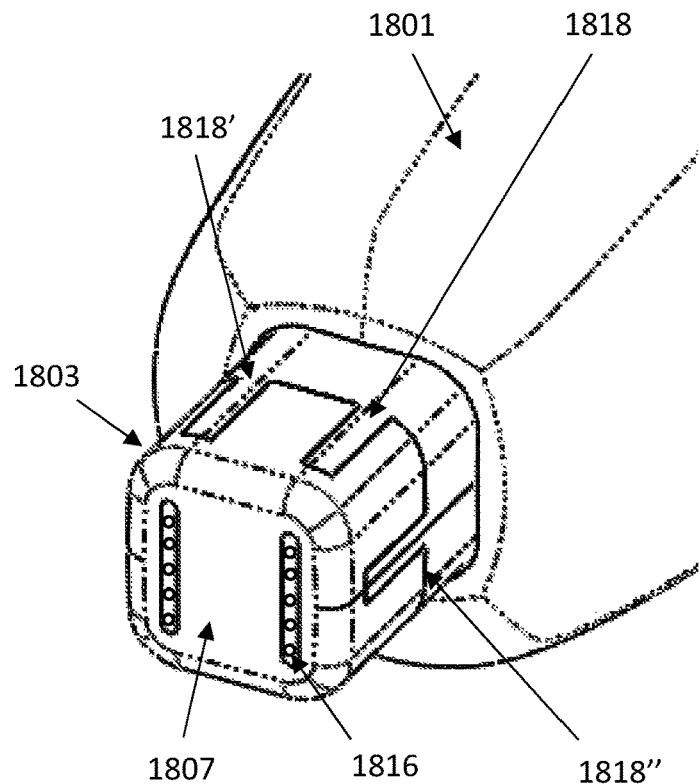
FIGS. 18A-18B illustrate an example of the retractable or protected needle electrodes.
Figure 18B:
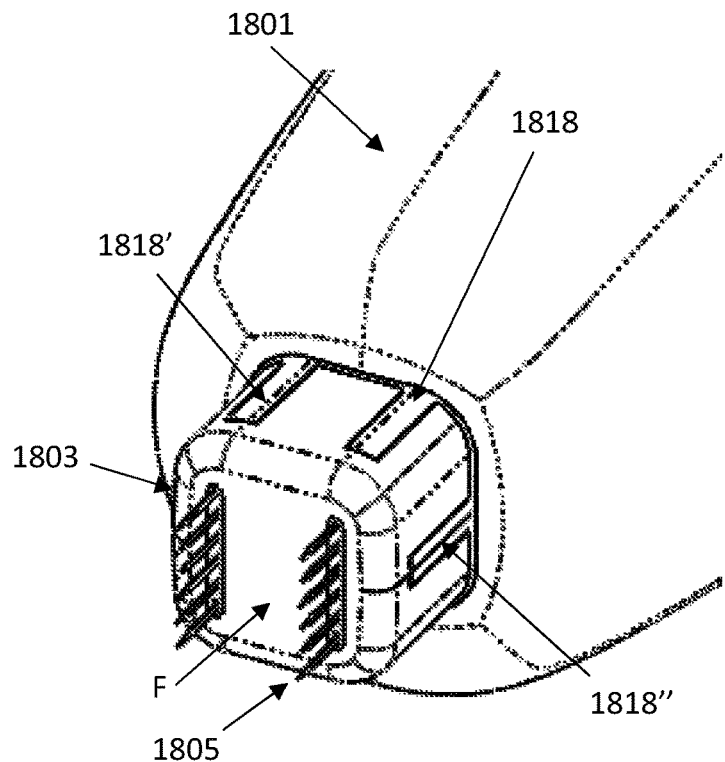

FIGS. 18A and 18B illustrate an example of an applicator tip having a retractable housing that may be insulating. In FIG. 18A the distal end of the applicator tip is shown with the electrode housing 1803 fully extended distally. An internal spring (not shown) may bias the electrode housing distally, holding it in an un-deployed configuration and providing a bias return force to restore the un-deployed configuration. The electrode housing may include a distal insulating cover 1807 that, in this example, has a plurality of openings or holes 1816 through which treatment electrodes 1805 may extend when the housing is pushed (by a force greater than the threshold force, in this example a biasing force) into the distal end of the applicator tip housing 1801. In this example the side of the electrode housing may include one or more fiducial markers 1818 that mark the relative position of the electrode housing relative to the applicator tip housing 1801 and/or the relative position and orientation of the treatment electrodes on the tip. For example, in FIGS. 18A and 18B, the two fiducial lines 1818, 1818' on the tops of the electrode housing 1803 are aligned with the rows of needle electrodes once they exit the electrode housing. In this way, the user may know where the rows of needle electrodes are. The fiducial line 1818" on the adjacent side is in the middle of the two rows of needles. The top of these lines may indicate the fully retracted position of the electrode housing and/or the fully extended position of the needle electrodes when deployed. Some or all of these fiducial markers (e.g., lines) on the electrode housing, or other markers on the electrode housing, may show how far the electrode housing is retracted, and/or how far the electrodes have been inserted into the tissue. For example, lines transverse to the elongate length (e.g., of fiducial lines 1818, 1818', 1818") may include indicators for the electrode depth. The fiducial markers described in reference to FIGS. 18A and 18B may be used in any of the examples, embodiments and implementations described herein. The distal end of the electrode housing may be covered by an insulating material that includes holes or opening through which the electrodes may extend when the electrode housing is pushed proximally. In some variations the insulating cover does not include holes or openings and instead the treatment electrodes penetrate into and through the soft insulating cover itself. For example, the soft insulting cover may be silicone, santoprene, or other TPE (Thermoplastic Elastomer) materials. The applicator tips, with retractable and insulating housings, may be formed of any appropriate size, including the 1.5 mm×1.5 mm, 2.5 mm×2.5 mm, 5 mm×5 mm, etc., dimensions.

Figures 28A, 28B, 28C, 28D:
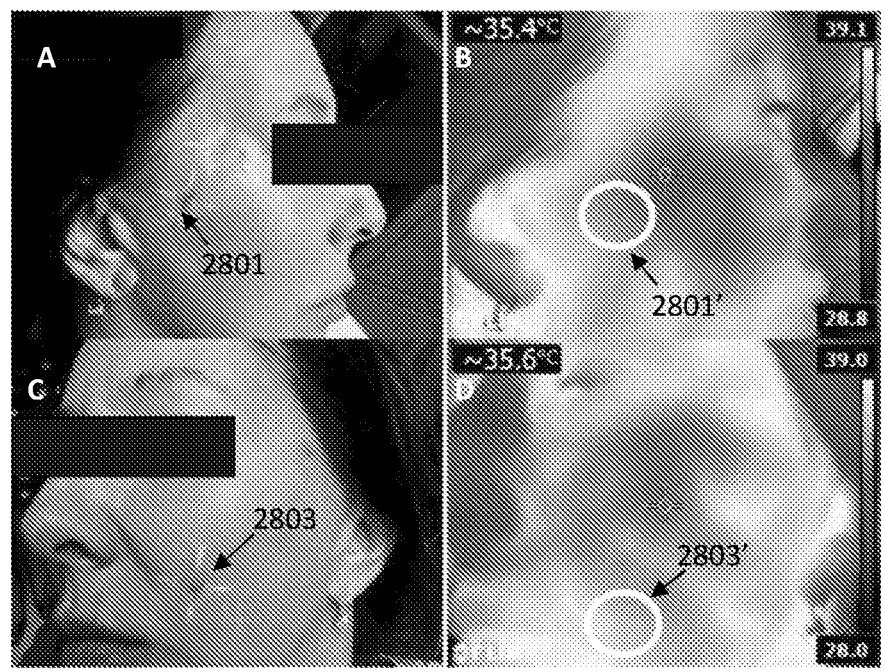
FIGS. 28A-28D show that there is a negligible change in tissue temperature following the treatments described herein.

As mentioned above, the methods and apparatuses described herein may provide non-thermal methods for treating the skin, e.g., to remove or modify a gland, including to treat a condition related to a gland, such as sebaceous hyperplasia. This is illustrated, for example, in FIGS. 28A-28D, showing a patient immediately (e.g., within 30 seconds) of receiving treatment on the face. In FIG. 28A, pulsed electrical energy having a pulse duration in sub-microsecond pulse range was applied to a treatment region 2801, as shown in a visible light camera view. In FIG. 28B, the same region 2801' of the face is shown by a concurrently-taken thermogram; the temperature of this region is not detectably elevated, compared to other region of the face. FIGS. 28C and 28D show visible light and thermogram images taken from a similar region of the left side of the patient's face. The treatment region 2803, 2803' does not show any appreciable change in temperature.

In any of the method and apparatuses described here, it may be beneficial to limit the energy applied to reduce side effects, such as hyperpigmentation and/or volume loss. Thus, although higher applied energy may result in an increase in efficacy, in some cases the lower energy may be acceptably effective in modifying or eliminating a gland, without further modifying the surrounding skin, which may lead to side effect such as hyperpigmentation and/or volume loss.

Figure 29:
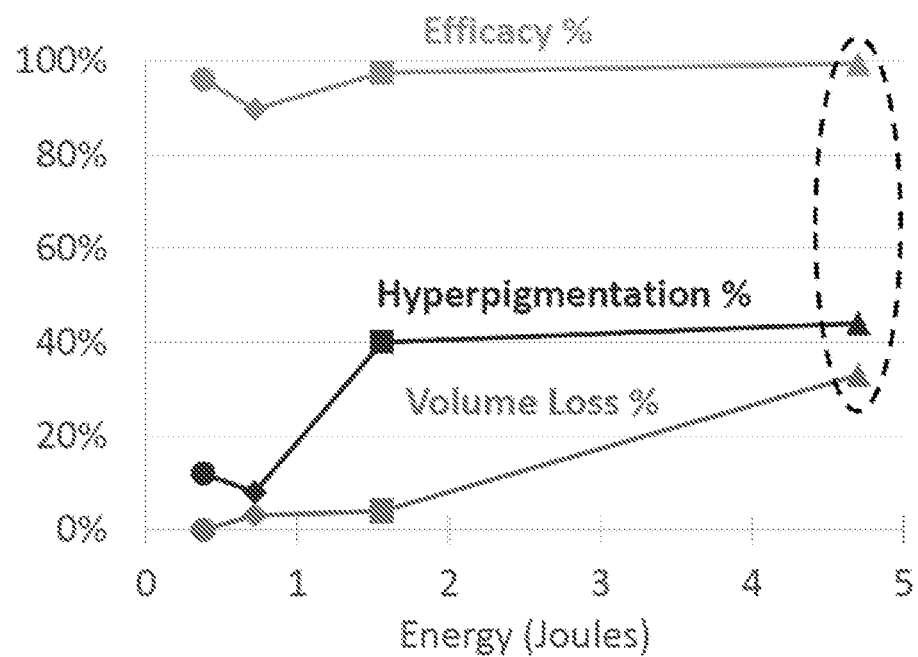
FIG. 29 is a graph showing the percentage of efficacy, hyperpigmentation, and volume loss with increasing applied energy for a 2.5×2.5 mm tip.
Figures 30, 31:
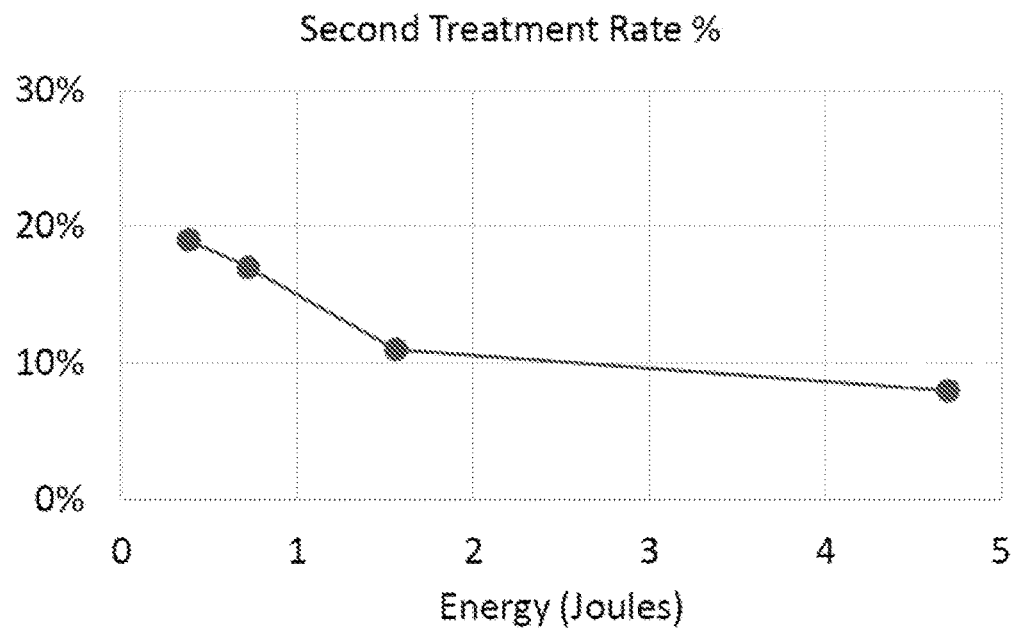
FIG. 30 is a graph showing the rate of second treatments at different applied energy fora 2.5×2.5 mm tip.
FIG. 31 is a table showing the results of sebaceous hyperplasia (SH) treatment in a dosage study looking at the effects of low to mid-level energy levels in treating SH.

For example, FIGS. 29-30 illustrates the results of 330 treated sebaceous hyperplasia lesions from 66 subjects, receiving one or two treatments, providing a titration of the energy dosage applied. In this study, patients were treated by inserting a plurality of electrodes from an applicator (such as illustrated in FIGS. 18A-18B described above) into a subject's skin so that a region of skin including a target gland was between two or more of the plurality of electrodes. Pulsed electrical energy having a pulse duration in sub-microsecond pulse range was then applied between the electrodes to eliminate the target gland. Energy dosages were varied between 0.4 J to 5 J (and could be combined with earlier, similarly acquired data at higher energy). Patients were tracked for 90 days and examined immediately following the procedure, 7 days following the procedure, 30 days following the procedure, 60 days following the procedure, and 90 days following the procedure. From these experiments up to 98% of the sebaceous hyperplasia lesions were rated as "clear" or "mostly clear" following a single treatment, even at the lower treatment power (e.g., 0.4 J, 0.7 J, 1.6 J, etc.), comparable with high-power treatments (e.g., 5 J or greater). The table shown in FIG. 31 illustrates results at sixty days, showing that for a 2.5 mm×2.5 mm tip ("spot size"), the efficacy for even the lower power treatments was >90% following a single treatment. (Note that the smaller sample size of 14 lesions for the 3.1 J disqualified this last row of data point from drawing conclusions).

The results of this dose study showed even for the lower-powered treatment levels, that the overall efficiency was greater than 90 percent. Interestingly, as shown in FIG. 29, although there was a slight decrease in efficacy at the lower powers (e.g., between 0.4 J and 1.6 J), both hyperpigmentation and volume loss was significantly reduced at these same lower powers. Note that for a 2.5×2.5 mm treatment tip treating a volume of 12.5 $mm^3$, 0.4 J and 1.6 J results in an energy density of 0.032 $J/mm^3$ and 0.128 $J/mm^3$. As shown in FIG. 29, at the two lowest powers applied (0.4 and 0.7 J), less than 20% of the treated lesions showed appreciable hyperpigmentation and less than 10% of the treated lesions showed appreciable volume loss. Above 1.6 J of applied power using the 2.5 mm×2.5 mm treatment tip and the hyperpigmentation increased above 40%. Between 1.6 J and 4.8 J the volume loss increase to greater than 30%, the hyperpigmentation rose above 40% and there was only a very slight increase in efficacy. For example, if the peak energy is limited to about 0.128 $J/mm^3$ or less, the hyperpigmentation may be less than 40% and the volume loss is less than about 5%, while the efficiency is greater than about 90%. Alternatively, if the peak energy is limited to about 0.08 $J/mm^3$ or less (e.g., 0.072 $J/mm^3$ or less, 0.064 $J/mm^3$ or less, 0.056 $J/mm^3$ or less, etc.), the hyperpigmentation may be less than 20% and the volume loss is less than about 5%, while the efficiency remains greater than about 90% (92% or more, 93% or more, 94% or more, 95% or more, etc.).

Thus, in some variations it may be beneficial to limit the applied energy when treating the skin to eliminate (or reduce the size or a number of) target glands within a target region by applying pulsed electrical energy having a pulse duration in sub-microsecond pulse range. For example, it may be beneficial to limit the applied energy during a treatment dose to 0.128 $J/mm^3$ or less (e.g., 0.112 $J/mm^3$ or less, 0.104 $J/mm^3$ or less, 0.100 $J/mm^3$ or less, 0.096 $J/mm^3$ or less, 0.088 $J/mm^3$ or less, 0.08 $J/mm^3$ or less, 0.072 $J/mm^3$ or less, 0.064 $J/mm^3$ or less, 0.056 $J/mm^3$ or less, etc.). Thus, lower treatment levels may provide high efficiency with reduced risks of undesirable side effect such as hyperpigmentation and volume loss.

Furthermore, the slightly lower efficiency at these lower power levels may still be greater than about 85% effective (e.g., may eliminate target glands, and/or treat target SH lesions in about 85% or more of the treated target tissue). In cases in which a first low-power treatment was unsuccessful the first time, a second follow-up treatment may be performed after a waiting period. The waiting period may be, for example one week, one month (e.g., 30 days), 60 days, 90 days, or more, as described above. FIG. 30 shows a graph showing the second treatment rate percentage from the same data set described above. As mentioned, although the lower energy pulsed sub-microsecond pulse range electrical energy resulted in a slightly higher rate of second treatments (e.g., between 20%-10% for applied energy of between 0.7 J and 1.6 J using a 2.5×2.5 mm tip, or between approximately 0.056 $J/mm^3$ and 0.128 $J/mm^3$), as described in FIG. 29, the greatly reduced rate of hyperpigmentation and a lower volume loss as compared to a dose of applied energy greater than 0.128 $J/mm^3$ makes the use of lower energy dose treatments desirable.

The threshold at which the efficacy remains high while the undesirable side effects such as hyperpigmentation and volume loss remain low when treating the skin as described herein may be a function of the applied energy density. For example, for a 2.5 mm×2.5 mm array or needle electrodes (described above), the threshold for the total energy applied may be between about 0.7 J and 1.6 J (e.g., about 1.5 J or less, about 1.4 J or less, about 1.3 J or less, about 1.2 J or less, about 1.1 J or less, about 1 J or less, etc.). Assuming a thickness of about 2 mm (e.g. penetration of about 2 mm), this threshold may be normalized to an energy density of between about 0.056 $J/mm^3$ and 0.128 $J/mm^3$ (e.g., about 0.12 $J/mm^3$ or less, about 0.112 $J/mm^3$ or less, about 0.104 $J/mm^3$ or less, about 0.096 $J/mm^3$ or less, about 0.088 $J/mm^3$ or less, about 0.08 $J/mm^3$ or less, etc.) for an array, such as an array of electrodes forming a pattern having a width and a height of between 1.4 mm and 5.5 mm.

Embodiments of the methods of the present disclosure may be implemented using computer software, firmware or hardware. Various programming languages and operating systems may be used to implement the present disclosure. The program that runs the method and system may include a separate program code including a set of instructions for performing a desired operation or may include a plurality of modules that perform such sub-operations of an operation or may be part of a single module of a larger program providing the operation. The modular construction facilitates adding, deleting, updating and/or amending the modules therein and/or features within the modules.

In some embodiments, a user may select a particular method or embodiment of this application, and the processor will run a program or algorithm associated with the selected method. In certain embodiments, various types of position sensors may be used. For example, in certain embodiment, a non-optical encoder may be used where a voltage level or polarity may be adjusted as a function of encoder signal feedback to achieve a desired angle, speed, or force.

Certain embodiments may relate to a machine-readable medium (e.g., computer readable media) or computer program products that include program instructions and/or data (including data structures) for performing various computer-implemented operations. A machine-readable medium may be used to store software and data which causes the system to perform methods of the present disclosure. The above-mentioned machine-readable medium may include any suitable medium capable of storing and transmitting information in a form accessible by processing device, for example, a computer. Some examples of the machine-readable medium include, but not limited to, magnetic disc storage such as hard disks, floppy disks, magnetic tapes. It may also include a flash memory device, optical storage, random access memory, etc. The data and program instructions may also be embodied on a carrier wave or other transport medium. Examples of program instructions include both machine code, such as produced by a compiler, and files containing higher level code that may be executed using an interpreter.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to perform or control performing of any of the steps, including but not limited to: displaying, communicating with the user, analyzing, modifying parameters (including timing, frequency, intensity, etc.), determining, alerting, or the like. In some exemplary embodiments hardware may be used in combination with software instructions to implement the present disclosure.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting. For example, as used herein, the singular forms "a", "an" and "the" are intended to include the plural forms as well, unless the context clearly indicates otherwise. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present apparatuses and methods.

The terms "comprises" and/or "comprising," when used in this specification (including the claims), specify the presence of stated features, steps, operations, elements, and/or components, but do not preclude the presence or addition of one or more other features, steps, operations, elements, components, and/or groups thereof. Unless the context requires otherwise, "comprise", and variations such as "comprises" and "comprising," means various components can be co-jointly employed in the methods and articles (e.g., compositions and apparatuses including device and methods). For example, the term "comprising" will be understood to imply the inclusion of any stated elements or steps but not the exclusion of any other elements or steps.

Any of the apparatuses and methods described herein may include all or a sub-set of the components and/or steps, and these components or steps may be either non-exclusive (e.g., may include additional components and/or steps) or in some variations may be exclusive, and therefore may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the disclosure as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the apparatuses and methods as it is set forth in the claims.

Various embodiments may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A system comprising:
   a pulse generator configured to generate non-thermal electrical pulses having an amplitude of at least 0.1 kV and a duration of less than 1000 nanoseconds;
   an applicator comprising a treatment tip having a plurality of needle electrodes, wherein each needle electrode of the plurality of needle electrodes comprises an uninsulated portion extending from an end of an insulated portion to a distal end of each needle electrode; and
   a controller coupled to the pulse generator and configured to apply a treatment dose from the plurality of needle electrodes to eliminate or reduce a size of a target gland within a subject 's skin, wherein the treatment dose provides an energy density of 1.5 J/mm$^3$ or less sufficient to eliminate or reduce the size of the target gland by selectively and non-thermally disrupting nuclei, organelles or outer membranes of cells of the target gland without permanently damaging structures outside the target gland.

2. The system of claim 1, wherein the controller regulates the treatment dose to be up to about 0.9 J/mm$^3$, wherein the plurality of needle electrodes forms a pattern having a width and a height of between 1.4 mm and 5.5 mm.

3. The system of claim 1, wherein the controller is configured to regulate the treatment dose to have an energy density of between 0.1 J/mm$^3$ and about 0.128 J/mm$^3$.

4. The system of claim 1, wherein the plurality of needle electrodes is arranged in an array having an area of between 2.25 mm$^2$ and 100 mm$^2$.

5. The system of claim 1, wherein the treatment tip comprises a retractable treatment tip housing configured to retract to expose the needle electrodes.

6. The system of claim 1, wherein the insulated portion of at least some of the needle electrodes extends between 0.1 mm and up to about 1 mm from a base of the treatment tip.

7. The system of claim 1, wherein the uninsulated portion of at least some of the needle electrodes extends between 1 mm and 4 mm from the insulated portion.

8. The system of claim 1, wherein the controller is configured to regulate the treatment dose at least in part based on a user input.

9. The system of claim 1, wherein the controller is configured to regulate the treatment dose automatically, optionally, based on a target treatment protocol.

10. The system of claim 1, wherein the target gland is at least one of a sebaceous gland, an eccrine gland, or an apocrine gland.

11. The system of claim 1, wherein the system is configured to treat one or more of the following conditions: acne, oily skin, sebaceous hyperplasia, rosacea, rosacea-like dermatitis, lupus miliaris disseminatus faciei (LMDF), xerosis, asteatosis, seborrhea, seborrheic dermatitis, seborrheic-like psoriasis, steatocystoma, hyperhidrosis, bromhidrosis, osmidrosis, chromhidrosis, hidradenitis suppurativa, Fox Fordyce disease, Frey's syndrome, cysts of the gland, and gland tumors.

12. The system of claim 1, wherein the system is a robotic system.

13. The system of claim 1, wherein the applicator is coupled to a robotic arm and the controller is configured to operate the robotic arm to place the applicator relative to the target gland.

14. A system comprising:
    a pulse generator configured to generate non-thermal electrical pulses having an amplitude of at least 0.1 kV and a duration of less than 1000 nanoseconds;
    an applicator comprising a treatment tip having a plurality of needle electrodes; and
    a controller coupled to the pulse generator and configured to apply a treatment dose from the plurality of needle electrodes to eliminate or reduce a size of a target gland within a subject 's skin by selectively and non-thermally disrupting nuclei, organelles or outer membranes of cells of the target gland, wherein the controller regulates the treatment dose to have a maximum energy density of 1.5 J/mm$^3$ or less.

15. A method comprising:
    positioning a plurality of needle electrodes so that a target gland in a region of a subject's skin is between two or more electrodes of the plurality of electrodes;
    and applying pulsed electrical energy having a pulse duration in sub-microsecond pulse range between the two or more electrodes of the plurality of electrodes, wherein the pulsed electrical energy has an amplitude of at least 0.1 kV and a duration of less than 1000 nanoseconds; wherein the pulsed electrical energy provides an energy density of 1.5 J/mm$^3$ or less, sufficient to eliminate or reduce the size of the target gland by selectively and non-thermally disrupting nuclei.

16. The method of claim 15, further comprising applying the pulsed electrical energy at an energy density of less than 0.128 J/mm$^3$.

17. The method of claim 15, wherein the positioning the plurality of electrodes comprises inserting the plurality of electrodes into the region between 1 mm and 5 mm deep.

18. The method of claim 15, the method comprising inserting an insulated portion of each of the needle electrodes to extend between 0.1 and 4 mm into a tissue to position an uninsulated portion of the needle electrodes at a depth of the target gland.

19. The method of claim 15, wherein a tissue outside the the target gland comprises at least one of: a portion of epidermis above the target gland, a portion of epidermis adjacent the target gland, one or more portions of dermis adjacent the one or more target glands.

20. The method of claim 15, wherein the one or more target glands is at least one of a sebaceous gland, an eccrine gland, or an apocrine gland and wherein the method is a method of treating one or more of the following conditions: acne, oily skin, sebaceous hyperplasia, rosacea, rosacea-like dermatitis, lupus miliaris disseminatus faciei (LMDF), xerosis, asteatosis, seborrhea, seborrheic dermatitis, seborrheic-like psoriasis, steatocystoma, hyperhidrosis, bromhidrosis, osmidrosis, chromhidrosis, hidradenitis suppurativa, Fox Fordyce disease, Frey's syndrome, cysts of the gland, and gland tumors.

21. The method of claim 15, wherein applying the pulsed electrical energy comprises applying for less than 5 minutes.

22. The method of claim 15, wherein the eliminating the target gland comprises eliminating a full length of the target gland.

* * * * *

UNITED STATES PATENT AND TRADEMARK OFFICE
CERTIFICATE OF CORRECTION

PATENT NO. : 12,178,496 B2
APPLICATION NO. : 17/284029
DATED : December 31, 2024
INVENTOR(S) : Lauren M. Jauregui Johnston et al.

Page 1 of 1

It is certified that error appears in the above-identified patent and that said Letters Patent is hereby corrected as shown below:

In the Claims

Claim 15, Column 38, Line 59; after "nuclei" insert --organelles or outer membranes of cells of the target gland without permanently damaging structures outside the target gland--.

Claim 19, Column 39, Line 4; after "outside" remove "the".

Claim 19, Column 39, Line 8; after "adjacent" remove "the one or more target glands" and insert --the target gland--.

Claim 20, Column 39, Lines 9-10; after "wherein" remove "the one or more target glands" and insert --the target gland--.

Signed and Sealed this
Sixth Day of May, 2025

Coke Morgan Stewart
*Acting Director of the United States Patent and Trademark Office*